(12) United States Patent
Jeraj et al.

(10) Patent No.: US 12,562,258 B2
(45) Date of Patent: Feb. 24, 2026

(54) METHODS AND SYSTEMS FOR ASSESSING TREATMENT OF A DISEASE BASED ON LESION FEATURES

(71) Applicant: Aiq Global Inc., Madison, WI (US)

(72) Inventors: Robert Jeraj, Madison, WI (US); Timothy Perk, Madison, WI (US); Stephen Yip, Madison, WI (US); S. Sean Houshmandi, Madison, WI (US)

(73) Assignee: AIQ Global Inc., Madison, WI (US)

( * ) Notice: Subject to any disclaimer, the term of this patent is extended or adjusted under 35 U.S.C. 154(b) by 714 days.

(21) Appl. No.: 17/865,770

(22) Filed: Jul. 15, 2022

(65) Prior Publication Data

US 2023/0046564 A1    Feb. 16, 2023

Related U.S. Application Data

(60) Provisional application No. 63/222,746, filed on Jul. 16, 2021.

(51) Int. Cl.
G06T 7/00 (2017.01)
G16H 30/40 (2018.01)
(52) U.S. Cl.
CPC ........... G16H 30/40 (2018.01); G06T 7/0012 (2013.01)
(58) Field of Classification Search
None
See application file for complete search history.

(56) References Cited

U.S. PATENT DOCUMENTS

| | | | |
|---|---|---|---|
| 9,161,720 B2 | 10/2015 | Jeraj et al. | |
| 9,603,567 B2 | 3/2017 | Jeraj et al. | |
| 10,445,878 B2 | 10/2019 | Jeraj et al. | |
| 2016/0100795 A1* | 4/2016 | Jeraj | A61B 5/0035 |
| | | | 600/431 |
| 2018/0333589 A1* | 11/2018 | Kim | G06T 7/0012 |
| 2019/0021677 A1* | 1/2019 | Grbic | G06T 7/11 |
| 2019/0221314 A1* | 7/2019 | Hennig | G06T 7/0012 |
| 2020/0226748 A1* | 7/2020 | Kaufman | G06T 7/194 |
| 2020/0380675 A1* | 12/2020 | Golden | G06T 7/0012 |

FOREIGN PATENT DOCUMENTS

| | | | |
|---|---|---|---|
| WO | WO 2020/069509 | 4/2020 | |
| WO | WO-2020069509 A1 * | 4/2020 | G06T 7/00 |
| WO | WO-2021108043 A1 * | 6/2021 | A61B 5/4848 |

OTHER PUBLICATIONS

International Search Report and Written Opinion for PCT/US2022/037277. Mailed Oct. 4, 2022. 14 pages.

(Continued)

*Primary Examiner* — Akwasi M Sarpong
*Assistant Examiner* — Pawan Dhingra
(74) *Attorney, Agent, or Firm* — Casimir Jones, S.C.; Kelly A. Barton

(57) ABSTRACT

The present disclosure provides methods, systems, and non-transitory computer-readable media for assessment of disease treatment or progression on a lesion-by-lesion level. The systems and methods are based on measurements of a variety of features including total number of lesions, total number and proportion of lesions regressing or progressing, changes in dimensions of a lesion over time, and uptake values of a molecular imaging agent.

14 Claims, 9 Drawing Sheets

• Imaging Data: single timepoint, dual timepoint, response
• Imaging Features: histogram measures, radiomics, response, heterogeneity
• Other Data: blood biomarkers, liquid biopsies, etc.

• Suitable models include: feature-based AI, deep learning, statistical models (e.g., Cox-pH)

• Risk Assessment
• Treatment Recommendations

(56) References Cited

OTHER PUBLICATIONS

Apolo et al., Prospective Study Evaluating Na18F PET/CT in Predicting Clinical Outcomes and Survival in Advanced Prostate Cancer. J Nucl Med. Jun. 2016;57(6):886-92.

Etchebehere et al., Prognostic Factors in Patients Treated with 223Ra: The Role of Skeletal Tumor Burden on Baseline 18F-Fluoride PET/CT in Predicting Overall Survival. J Nucl Med. Aug. 2015;56(8):1177-84.

Even-Sapir et al., 18F-Fluoride positron emission tomography and positron emission tomography/computed tomography. Semin Nucl Med. Nov. 2007;37(6):462-9.

Even-Sapir et al., Assessment of malignant skeletal disease: initial experience with 18F-fluoride PET/CT and comparison between 18F-fluoride PET and 18F-fluoride PET/CT. J Nucl Med. Feb. 2004;45(2):272-8.

Even-Sapir et al., The detection of bone metastases in patients with high-risk prostate cancer: 99mTc-MDP Planar bone scintigraphy, single- and multi-field-of-view SPECT, 18F-fluoride PET, and 18F-fluoride PET/CT. J Nucl Med. Feb. 2006;47(2):287-97.

Harmon et al., Quantitative Assessment of Early [18F]Sodium Fluoride Positron Emission Tomography/Computed Tomography Response to Treatment in Men With Metastatic Prostate Cancer to Bone. J Clin Oncol. Aug. 20, 2017;35(24):2829-2837.

Huynh et al., Associations of Radiomic Data Extracted from Static and Respiratory-Gated CT Scans with Disease Recurrence in Lung Cancer Patients Treated with SBRT. PLoS One. Jan. 3, 2017;12(1):e0169172. 17 pages.

Ishwaran et al., Random survival forests. Ann. Appl. Stat., 2008. 2(3): p. 841-860.

Kairemo et al., Development of sodium fluoride PET response criteria for solid tumours (NAFCIST) in a clinical trial of radium-223 in osteosarcoma: from RECIST to PERCIST to NAFCIST. ESMO Open. Feb. 28, 2019;4(1):e000439.

Kyriakopoulos et al., Exploring Spatial-Temporal Changes in 18F-Sodium Fluoride PET/CT and Circulating Tumor Cells in Metastatic Castration-Resistant Prostate Cancer Treated With Enzalutamide. J Clin Oncol. Nov. 1, 2020;38(31):3662-3671.

Lin et al., Repeatability of Quantitative 18F-NaF PET: A Multicenter Study. J Nucl Med. Dec. 2016;57(12):1872-1879.

Lin et al., Response-to-repeatability of quantitative imaging features for longitudinal response assessment. Phys Med Biol. Jan. 18, 2019;64(2):025019. 34 pages.

Lindgren Belal et al., 3D skeletal uptake of 18F sodium fluoride in PET/CT images is associated with overall survival in patients with prostate cancer. EJNMMI Res. Dec. 2017;7(1):15. 8 pages.

McNeel et al., Phase II Trial of a DNA Vaccine Encoding Prostatic Acid Phosphatase (pTVG-HP [MVI-816]) in Patients With Progressive, Nonmetastatic, Castration-Sensitive Prostate Cancer. J Clin Oncol. Dec. 20, 2019;37(36):3507-3517.

Morin et al., Metabolic Imaging of Prostate Cancer Reveals Intrapatient Intermetastasis Response Heterogeneity to Systemic Therapy. Eur Urol Focus. Dec. 2017;3(6):639-642.

Perk et al., A statistically optimized regional thresholding method (SORT) for bone lesion detection in 18F-NaF PET/CT imaging. Phys Med Biol. Nov. 20, 2018;63(22):225018. 1-10.

Perk et al., Automated classification of benign and malignant lesions in 18F-NaF PET/CT images using machine learning. Phys Med Biol. Nov. 20, 2018;63(22):225019. 1-12.

Polsterl. scikit-survival: A Library for Time-to-Event Analysis Built on Top of scikit-learn. Journal of Machine Learning Research. 2020, 21, p. 1-6.

Rescigno et al., Early changes in PSA and association with outcomes in mCRPC patients. JCO, 2018, 36(15_suppl) 5063-5063.

Roth et al., Anatomic Heterogeneity in Metastatic Castrate Resistant Prostate Cancer. Medical Physics, 2017. 44(6): p. 3252-3252.

Roth et al., Impact of Anatomic Location of Bone Metastases on Prognosis in Metastatic Castration-Resistant Prostate Cancer. Clin Genitourin Cancer. Aug. 2019;17(4):306-314.

Scher et al., Design and end points of clinical trials for patients with progressive prostate cancer and castrate levels of testosterone: recommendations of the Prostate Cancer Clinical Trials Working Group. J Clin Oncol. Mar. 1, 2008;26(7):1148-59.

Scher et al., Trial Design and Objectives for Castration-Resistant Prostate Cancer: Updated Recommendations From the Prostate Cancer Clinical Trials Working Group 3. J Clin Oncol. Apr. 20, 2016;34(12):1402-18.

Svetnik et al., Random forest: a classification and regression tool for compound classification and QSAR modeling. J Chem Inf Comput Sci. Nov.-Dec. 2003;43(6):1947-58.

Wahl et al., From RECIST to PERCIST: Evolving Considerations for PET response criteria in solid tumors. J Nucl Med. May 2009;50 Suppl 1 (Suppl 1):122S-50S.

Wang et al., Study on the distribution features of bone metastases in prostate cancer. Nucl Med Commun. Apr. 2012;33(4):379-83.

Yip et al., Development and evaluation of an articulated registration algorithm for human skeleton registration. Phys Med Biol. Mar. 21, 2014;59(6):1485-99.

Yip et al., Use of articulated registration for response assessment of individual metastatic bone lesions. Phys Med Biol. Mar. 21, 2014;59(6):1501-14.

* cited by examiner

1

METHODS AND SYSTEMS FOR ASSESSING TREATMENT OF A DISEASE BASED ON LESION FEATURES

CROSS-REFERENCE TO RELATED APPLICATIONS

This application claims the benefit of U.S. Provisional Application No. 63/222,746, filed Jul. 16, 2021, the content of which is herein incorporated by reference in its entirety.

FIELD

The present disclosure provides computer-implemented methods, systems, and non-transitory computer-readable media for assessment of disease treatment on a lesion-by-lesion level.

BACKGROUND

Late stage cancer patients may present with hundreds of lesions (e.g., bone metastases in bone metastatic prostate cancer (mPC)). Treatment benefit in these patients may be monitored using a combination of $^{99m}$Tc-methylene diphosphonate (MDP) planar scintigraphy (bone scans); chest, abdomen, and pelvic CT scans; serum prostate specific antigen (PSA); and clinical symptoms. Previous recommendations define progression based on the appearance of new lesions on scans verified by follow-up (e.g., the 2+2 rule). However, due to the complexity of assessing patients with many lesions, the determination of progression has shifted to be based primarily on physician discretion. Further recommendations that factor in all information gathered from a patient in a quantitative approach could provide essential information to aid in assisting and standardizing physician decision making.

Molecular imaging, for example, with positron emission tomography and computed tomography (PET/CT) imaging has been considered for providing the information needed for this comprehensive approach. Molecular imaging with different molecular imaging agents, such as $^{18}$F-sodium fluoride PET/CT (NaF) imaging has been shown to have superior sensitivity for detecting bone metastases compared to MDP bone scans. Multiple studies have shown the prognostic power of molecular imaging metrics, at both a single timepoint (either baseline or at follow-up) or by measuring changes across timepoints.

Within a population of mCRPC patients, substantial inter-lesion response heterogeneity was found, with patients having at least one progressing and responding lesion at the same time. This characteristic of mPC was confirmed using FDG PET/CT imaging. Heterogeneity in how lesions within the same patient respond confound the use of single patient metrics to fully understand what drives patient outcome.

SUMMARY

This disclosure relates to computer-implemented methods and non-transitory computer-readable media assessing treatment and progression of a disease in a subject. In some embodiments, the disease is cancer.

In some embodiments, the methods comprise acquiring a first imaging scan of the subject wherein the imaging scan is configured to identify and segment lesions in the subject; processing the scan to: identify locations of the lesions, quantify the lesions in the subject, and calculate an imaging signal for at least one imaging feature of each lesion; and providing a disease treatment assessment score based on evaluation of the imaging signal for features directed to individual lesions, for features that consider differences in imaging signals across any combination or all lesions in the subject, or a combination thereof.

In some embodiments, the features directed to individual lesions from the first scan comprise total number of lesions, highest lesion imaging signal, average lesion imaging signal, total lesion imaging signal, size and/or volume of each lesion, and combinations thereof in the subject. In some embodiments, the features directed to individual lesions from the first scan comprise total number of lesions, highest lesion imaging signal, and total lesion imaging signal in the subject. In select embodiments, the features directed to individual lesions from the first scan comprise all lesions in the subject.

In some embodiments, the features that consider differences in imaging signals across different lesions from the first scan comprise one or more textural features of maximum, mean, and total imaging signal between the different lesions.

In some embodiments, acquiring the first imaging scan comprises acquiring a scan of a molecular imaging agent in the subject wherein the molecular imaging agent is configured to segment or target lesions.

In some embodiments, processing the first imaging scan comprises calculating uptake values of the molecular imaging agent for each lesion and the disease treatment assessment score comprises evaluation of the uptake values for features directed to individual lesions, for features that consider differences in uptake values across any combination or all lesions in the subject, or a combination thereof. In some embodiments, the features directed to individual lesions from the first scan comprise total number of lesions, maximum lesion uptake, mean lesion uptake, total lesion uptake, and combinations thereof in the subject. In some embodiments, the features that consider differences in uptake values across different lesions from the first scan comprise standard deviation, skewness, kurtosis, and combinations thereof of maximum lesion uptake, mean lesion uptake, total lesion uptake between the different lesions.

The methods may further comprise acquiring a second imaging scan of the subject wherein the imaging scan is configured to identify and segment lesions, wherein the first scan and second scan are separated by a period of time; and processing the second scan to: identify locations of the lesions, quantify the lesions in the subject, and calculate an imaging signal for at least one imaging feature of each lesion; determine homologous lesions between the first and second scans and measure a change in each corresponding imaging signal, classify each lesion based on the change in each lesion; and providing a disease treatment assessment score based on evaluation of the imaging signal from the first or second scan for features directed to individual lesions or for features that consider differences in imaging signals across any combination or all lesions in the subject from the second scan, the change in features directed to individual lesions between the first and second scans, the change in features that consider differences in at least one imaging signal across different lesions for homologous lesions between the first and second scans, or a combination thereof. In some embodiments, each lesion is classified as completely responding (iCR), partially responding (iPR), stable (iSD), progressing (iPD), or new (iNL).

In some embodiments, the change in features directed to individual lesions from the second scan comprise: changes in total number of lesions, maximum, mean, and total imaging signal between the individual lesions and combinations thereof in the subject.

In some embodiments, the change in features that considers differences in imaging signals across different lesions from the second scan comprise: changes in one or more textural features of maximum, mean, and total imaging signal between the different lesions. In certain embodiments, the change in features that consider differences in imaging signals across different lesions from the second scan comprise: changes in standard deviations for maximum, mean, and total imaging signal between the different lesions in a single scan; standard deviations of the change in maximum, mean, and total imaging signal; standard deviations for skewness and kurtosis for maximum, mean, and total imaging signal; total number of lesions classified as completely responding (iCR), partially responding (iPR), stable (iSD), progressing (iPD), or new (iNL); sum of lesions classified as completely responding (iCR) and partially responding (iPR); proportion of the total number of lesions classified in each of completely responding (iCR), partially responding (iPR), stable (iSD), progressing (iPD), or new (iNL); proportion of the total number of lesions classified as completely responding (iCR) and partially responding (iPR); proportion of the total number of lesions classified as progressing (iPD) and new (iNL); standard deviations of the change in maximum, mean, and total imaging signal for lesions classified as progressing (iPD); standard deviations of the change in maximum, mean, and total imaging signal for lesions classified as partially responding (iPR); standard deviations of the mean imaging signal from first scan of lesions classified as progressing (iPD) following second scan, standard deviations of the mean imaging signal of lesions classified as progressing (iPD) and new (iNL), and the percent change between the two; standard deviations of the mean imaging signal from first scan of lesions classified as completely responding (iCR) and partially responding (iPR) following second scan, standard deviations of the mean imaging signal of lesions classified as partially responding (iPR), and the percent change between the two; maximum, mean, and total imaging signal in the subject of lesions classified as progressing (iPD) from first scan following second scan, maximum, mean, and total imaging signal in the subject of lesions from the second scan classified as progressing (iPD) and new (iNL), and the percent change between the two; maximum, mean, and total imaging signal in the subject of lesions classified as completely responding (iCR) and partially responding (iPR) from first scan following second scan, maximum, mean, and total imaging signal in the subject of lesions from the second scan classified as partially responding (iPR), and the percent change between the two; and combinations thereof. In select embodiments, the change in features that consider differences in imaging signals across different lesions comprise: total number of lesions classified as progressing (iPD) or new (iNL); standard deviations of the change in maximum, mean, and total imaging signal for lesions classified as progressing (iPD); standard deviations of the mean imaging signal from first scan of lesions classified as progressing (iPD) following second scan; standard deviations of the mean imaging signal of lesions classified as progressing (iPD) and new (iNL); maximum and total imaging signal in the subject of lesions classified as progressing (iPD) from first scan following second scan; maximum and total imaging signal in the subject of lesions from the second scan classified as progressing (iPD) and new (iNL); mean imaging signal in the subject of lesions from the second scan classified as progressing (iPD) and new (iNL); and combinations thereof.

In some embodiments, acquiring the second imaging scan comprises acquiring a scan of molecular imaging agent in the subject wherein the molecular imaging agent is configured to target or segment lesions. In some embodiments, processing the second scan comprises calculating uptake values of the molecular imaging agent for each lesion and the disease treatment assessment score comprises a change in features that consider differences in uptake values across different lesions for homologous lesions.

In some embodiments, the change in features directed to individual lesions from the second scan comprises changes in total number of lesions, maximum lesion uptake, mean lesion uptake, total lesion uptake, and combinations thereof in the subject. In certain embodiments, the change in features that consider differences in uptake values across different lesions from the second scan comprise: changes in standard deviations for maximum lesion uptake, mean lesion uptake, total lesion uptake between the different lesions in a single scan; standard deviations of the change in maximum lesion uptake, mean lesion uptake, total lesion uptake; standard deviations for skewness and kurtosis for maximum lesion uptake, mean lesion uptake, total lesion uptake; total number of lesions classified as completely responding (iCR), partially responding (iPR), stable (iSD), progressing (iPD), or new (iNL); sum of lesions classified as completely responding (iCR) and partially responding (iPR); proportion of the total number of lesions classified in each of completely responding (iCR), partially responding (iPR), stable (iSD), progressing (iPD), or new (iNL); proportion of the total number of lesions classified as completely responding (iCR) and partially responding (iPR); proportion of the total number of lesions classified as progressing (iPD) and new (iNL); standard deviations of the change in maximum lesion uptake, mean lesion uptake, total lesion uptake for lesions classified as progressing (iPD); standard deviations of the change in maximum lesion uptake, mean lesion uptake, total lesion uptake for lesions classified as partially responding (iPR); standard deviations of the mean lesion uptake from first scan of lesions classified as progressing (iPD) following second scan, standard deviations of the mean lesion uptake of lesions classified as progressing (iPD) and new (iNL), and the percent change between the two; standard deviations of the mean lesion uptake from first scan of lesions classified as completely responding (iCR) and partially responding (iPR) following second scan, standard deviations of the mean lesion uptake of lesions classified as partially responding (iPR), and the percent change between the two; maximum lesion uptake, mean lesion uptake, and total lesion uptake in the subject of lesions classified as progressing (iPD) from first scan following second scan, maximum lesion uptake, mean lesion uptake, and total lesion uptake in the subject of lesions from the second scan classified as progressing (iPD) and new (iNL), and the percent change between the two; maximum lesion uptake, mean lesion uptake, and total lesion uptake in the subject of lesions classified as completely responding (iCR) and partially responding (iPR) from first scan following second scan, maximum lesion uptake, mean lesion uptake, and total lesion uptake in the subject of lesions from the second scan classified as partially responding (iPR), and the percent change between the two; and combinations thereof.

In select embodiments, the change in features that consider differences in uptake across different lesions comprise: total number of lesions classified as progressing (iPD) or new (iNL); standard deviations of the change in maximum lesion uptake, mean lesion uptake, total lesion uptake for lesions classified as progressing (iPD); standard deviations of the mean lesion uptake from first scan of lesions classified as progressing (iPD) following second scan; standard deviations of the mean lesion uptake of lesions classified as progressing (iPD) and new (iNL); maximum lesion uptake and total lesion uptake in the subject of lesions classified as progressing (iPD) from first scan following second scan; maximum lesion uptake and total lesion uptake in the subject of lesions from the second scan classified as progressing (iPD) and new (iNL); mean lesion uptake in the subject of lesions from the second scan classified as progressing (iPD) and new (iNL); and combinations thereof.

The methods may further comprise acquiring at least one additional imaging scan of the subject wherein the imaging scan is configured to identify and segment lesions; and processing the at least one additional imaging scan to: identify locations of the lesions, quantify the lesions in the subject, and calculate an imaging signal for at least one imaging feature of each lesion; determine homologous lesions between any two imaging scans and measure a change in each corresponding imaging signal, classify each lesion based on the change in each lesion; and providing a disease treatment assessment score based on evaluation of the imaging signal directed to individual lesions or for features that consider differences in imaging signals across any combination or all lesions in the subject from the at least one additional imaging scan, the change in features directed to individual lesions between any two imaging scans, the change in features that consider differences in at least one imaging signal across different lesions for homologous lesions between any two imaging scans, or a combination thereof.

The methods may further comprise acquiring an anatomical scan. In some embodiments, the anatomical scan is acquired at the same time as the first scan. In some embodiments, the anatomical scan is acquired at the same time as the second scan. In some embodiments, the anatomical scan is acquired at the same time as the first scan and the second scan. In some embodiments, the methods further comprise classifying the lesions according to anatomical locations. In some embodiments, the disease treatment assessment score is further based on evaluation of anatomical locations of lesions, anatomical distribution of lesions, or a combination thereof.

In some embodiments, the disease treatment assessment score is further based on radiomics features.

In some embodiments, the disease treatment assessment score is further based on biomarker data.

In some embodiments, the disease treatment assessment score is a measure of duration of clinical benefit of the treatment (e.g., overall survival, progression free survival, decreases in lesion number and/or dimensions).

In some embodiments, the methods may further comprise providing a disease projection analysis based on simulations of disease treatment by removal of a specific lesion, or combination of lesions, or alteration of one or more imaging features representing successful treatment of a specific lesion, or combination of lesions, from a previous imaging scan.

Further disclosed herein are non-transitory computer-readable media storing instructions and system comprising the non-transitory computer-readable media and one or more processors that when executed perform the methods described herein.

Other aspects and embodiments of the disclosure will be apparent in light of the following detailed description and accompanying figures.

DETAILED DESCRIPTION

Figure 1A:
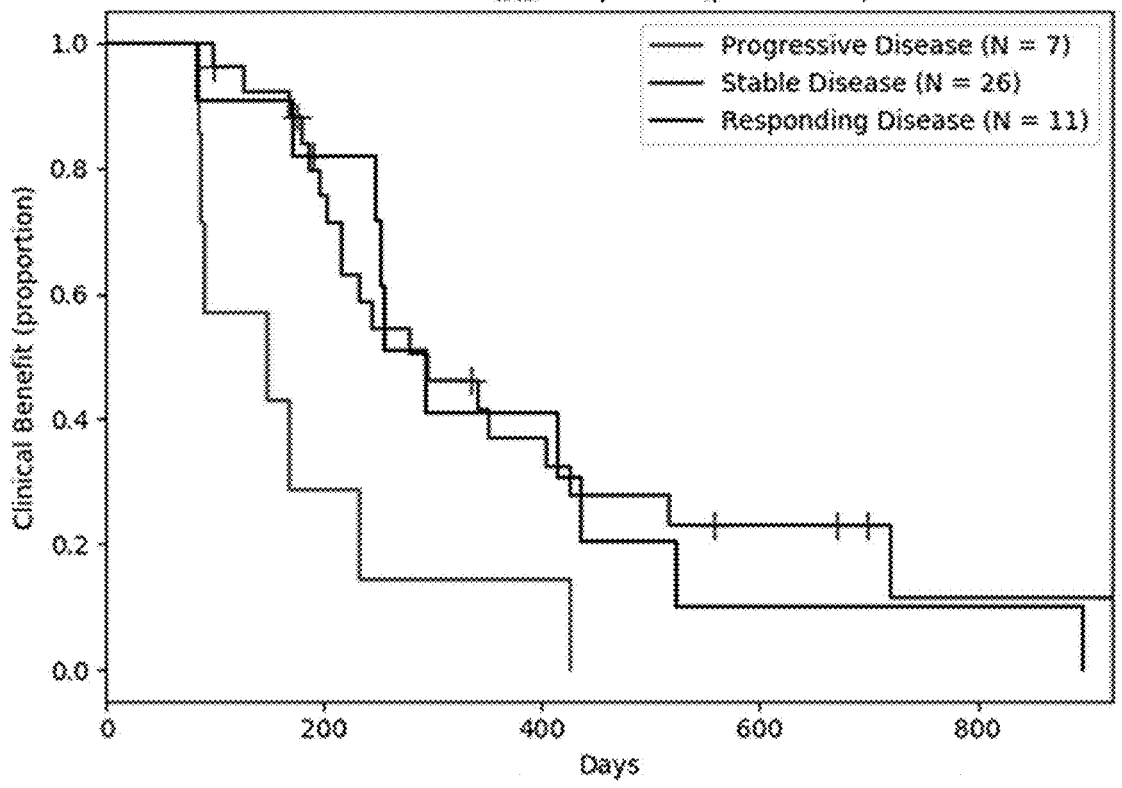
FIGS. 1A-1C are Kaplan-Meier curves for each clinical trial, as indicated, using the method described by Harmon et al. (J Clin Oncol, 2017. 35(24): p. 2829-2837, incorporated herein by reference) and the limits from Lin et al. (J Nucl Med, 2016. 57(12): p. 1872-1879, incorporated herein by reference) where patients are classified as having progressive disease ($\Delta SUV_{total}>44\%$), stable disease ($-30\%<\Delta SUV_{total}<44\%$), or partial response ($\Delta SUV_{total}<-30\%$).

The present disclosure provides methods and systems for assessing treatment of a disease based on features of lesions within the subject determined from an imaging scan.

Previous assessment methods were developed and tested within the same dataset. However, as shown herein, patient-level metrics that were shown to be predictive alone in previous studies were no longer predictive when applied to external datasets gathered with different imaging centers, scanners, and disease stages. In order to generalize predictions of duration of benefit, a machine learning model was trained with many features, as described herein, and this model predicted duration of clinical benefit in completely external datasets. The methods and systems described herein were able to predict patient outcomes in very different patient populations, acquired at different imaging centers, with different scanners and disease stages. Using data from highly metastatic patients on the second or third lines of systemic therapies like chemotherapy or AR-directed therapies, the methods and systems were able to predict which patients treated with a particular therapy would or would not have a sustained benefit.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific, and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

A "subject" may be human or non-human and may include either adults or juveniles (e.g., children). Moreover, subject may mean any living organism, preferably a mammal (e.g., human or non-human). Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment of the methods and compositions provided herein, the mammal is a human. "Subject" and "patient" may be used interchangeably herein.

A "biomarker" includes a biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the biological sample and that may be isolated from, or measured in, the biological sample (e.g., tissues, fluids, and cells). Furthermore, a biomarker may be the entire intact molecule, or a portion thereof that may be partially functional or recognized, for example, by an antibody or other specific binding protein. A biomarker may be associated with a given state of a subject, such as a particular stage of disease. In some embodiments, the biomarker is a cancer biomarker (e.g., circulating tumor DNA, protein biomarkers (e.g., prostate specific antigen, alpha-fetoprotein, carcinoembryonic antigen). A measurable aspect of a biomarker may include, for example, the presence, absence, or concentration of the biomarker in the biological sample from the subject and/or relative changes of any of the measurable aspects compared to a standard (e.g., internal or from a healthy subject). The measurable aspect may also be a ratio of two or more measurable aspects of two or more biomarkers. Biomarker, as used herein, also encompasses a biomarker profile comprising measurable aspects of two or more individual biomarkers. The two or more individual biomarkers may be from the same or different classes of biomarkers such as, for example, a nucleic acid and a carbohydrate, or may measure the same or different measurable aspect such as, for example, absence of one biomarker and concentration of another. A biomarker profile may comprise any number of individual biomarkers or features thereof. In another embodiment, the biomarker profile comprises at least one measurable aspect of at least one internal standard. Methods of identifying and quantifying biomarkers are well known in the art and include histological and molecular methods such as enzyme-linked immunosorbent assays (ELISA) and other immunoassays, gel electrophoresis, protein and DNA arrays, mass spectrometry, colorimetric assays, electrochemical assays, and fluorescence methods.

The term "contrast agent," as used herein, refers to an agent used to highlight specific areas, tissues, and/or biological fluids so that organs, blood vessels, tissues and/or lesions are more visible.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The present disclosure provides systems and methods for assessing disease progression and treatment in a subject. The methods comprise acquiring a first imaging scan of the subject wherein the imaging scan is configured to identify and segment lesions in the subject. In some embodiments, the imaging modality inherently allows segmentation of lesions such that the lesions are identifiable or distinguishable from surrounding tissues and organs of the subject. In some embodiments, the methods comprise acquiring a first imaging scan of the subject wherein a molecular imaging agent (e.g., a radioactive tracer, imaging probe, or contrast agent) segments or targets lesions. As used herein, "lesion" refers to a region in an organ or tissue which is abnormal or has suffered damage through injury or disease, such as a wound, ulcer, abscess, or tumor.

The imaging scan comprises any imaging modality which allow extraction of features from the resulting images (e.g., using data characterization algorithms). Examples of the types of imaging scan include, but are not limited to, CT, PET, SPECT, MRI, US, and the like. Generally, regardless of scan type, three-dimensional imaging data is preferred.

In some embodiments, the imaging modality may employ an imaging agent. The imaging agent may include any FDA approved imaging agent, such as those included in the Molecular Imagining Probes and Contrast Agents List provided in the Molecular Imaging and Contrast Agent Database (MICAD). Examples of types of imaging agents include, but are not limited to, fluorodeoxyglucose ($^{18}$F) (FDG) or variants thereof (e.g., 2-deoxy-2-$^{18}$F-fluoroglucose, 3'-deoxy-3'-[$^{18}$F]fluoro-L-thymidine (FLT)), Fluciclovine ($^{18}$F), or similar markers of cellular proliferation that quickly accumulates in proliferating cells (tumor or cancer cells); [$^{18}$F]DMPY2 PET, a marker for primary and metastatic melanomas; NaF, which is usually chosen for imaging of treatment response in metastatic bone lesions; $^{99m}$Tc-methoxyisobutylisonitrile ($^{99m}$Tc-sestamibi) and 16α-$^{18}$F-fluoro-17β-estradiol (FES) which accumulate in breast malignancies, [$^{18}$F]Galacto-RGD (an αvβ3-selective tracer) which is used as an imaging agent for anti-angiogenic therapy since the integrin αvβ3 plays a key role in angiogenesis; and contrast agents based on gadolinium (e.g., gadoterate meglumine (Gd-DOTA)). In some embodiments, an imaging agent may be attached to a biologically active molecules, the latter which offer specificity to a specific type of lesion. The nature of the imaging modality influences the selection of an imaging agent. For example, positron emission tomography (PET) can be used with FDG or NaF and SPECT (single-photon emission computed tomography) can be used with $^{99m}$Tc-sestamibi.

The disease may comprise any disease or disorder which can be monitored by molecular imaging lesion features, as described above. In some embodiments, the disease is cancer. The cancer may be any cancer. In some embodiments, the cancer is a solid tumor. In some embodiments, the cancer or cancer cell comprises lymphoma, cervical cancer, lung cancer (e.g., non-small-cell lung cancer and small-cell lung cancer), colorectal cancer, prostate cancer, bone cancer, ovarian cancer, breast cancer and/or leukemia.

The methods comprise processing the imaging scan to identify the locations of the lesions, quantify the lesions in the subject, and calculate an imaging signal for at least one imaging feature of each lesion (e.g., uptake values of an imaging agent). Processing of the scan may be completed using a computer implemented method. See for example, U.S. Pat. No. 10,445,878 and Perk et al. *Phys Med Biol.* 2018, each of which is incorporated herein by reference.

By using knowledge about the disease or suspected disease and, when appropriate, nature of the molecular imaging agent uptake and retention distribution, automatic lesion identification on many dispersed lesions can be accomplished with a high degree of accuracy. Automatic measurement of each distinguishable lesion allows analysis on a lesion-by-lesion level and provides an overall assessment of the disease and treatment of the subject, which may not be possible when analyzing only a subset of lesions.

One method for identifying lesions may involve evaluation against a threshold level, just above background image levels. Other identification techniques are contemplated including, for example, manual contouring in which an image analyst freehand contours colored molecular imaging data using a CT or MRI image as a guide when necessary, or circular contouring where an experienced physician adjusts the size of the circle around each lesion, or other automatic contouring techniques, such as uptake gradient based methods, or imaging feature-identifying methods.

The identification may account for normal variations in anatomical structures or tissues with respect to the imaging feature (e.g., rate of uptake and degree of uptake) of a specific tracer or specific image modality. The result is a normalized scan that better reveals lesion location, reducing subjective interpretation and improving the assessment of lesion-based differences. The identification and downstream processing may also segment the lesion from anatomical structures or tissues thus defining boundaries around the lesion after identification. By eliminating some tissues, and especially tissues that may indicate false positive uptakes, a more sensitive assessment of lesion or disease progression may be made when multiple diffuse lesions may be present. Overall, the identification process detects, refines, and defines the dimensions of the lesion (shape, size, volume).

After identification, and optionally, segmentation of each of the lesions, the total number of lesions may be determined and each identified lesion may be characterized by a number of features.

The methods comprise providing a disease treatment assessment score based on evaluation of the imaging signal for features directed to individual lesions, as discussed above, but also for features that consider differences in imaging signals across any combination or all lesions in the subject, or a combination thereof. Providing the disease treatment assessment score may comprise performing a multivariate survival analysis, including but not limited to Cox proportional hazards analysis and random survival forest analysis.

The disease treatment assessment score may provide a measure of duration of clinical benefit of the treatment. For example, the duration of clinical benefit of treatment may include: overall survival, disease-specific survival, disease-free survival, metastasis-free survival, progression free survival, decreases in lesion number and/or dimensions, changes in biomarker-based outcomes, and the like.

The features directed to individual lesions from the first scan may comprise: total number of lesions, highest lesion imaging signal, average lesion imaging signal, total lesion imaging signal, size and/or volume of each lesion, and combinations thereof in the subject (e.g., intensity (I), standardized uptake value (SUV), Hounsfield unit (HU)). In some embodiments, the features directed to individual lesions from the first scan comprise the total number of lesions in the subject. In some embodiments, the features directed to individual lesions from the first scan comprise the total number of lesions, highest lesion imaging signal, and total lesion imaging signal in the subject. In some embodiments, the features directed to individual lesions from the first scan comprise all lesions in the subject.

The features that consider differences in imaging signals across different lesions from the first scan may comprise one or more textural features. Textural features can include first-order features. First-order feature include, for example, intensity or magnitude, entropy, total signal, minimum signal, maximum signal, percentiles, mean, median, ranges, deviations (e.g., standard deviation, root mean square deviation) skewness, kurtosis, variance, uniformity. Textural features can also include shape features, including, but not limited to, volumes, surface area, sphericity or proportions, areas, perimeters, length, width, diameter. Textural features may also include any or all of second-order or higher-order statistical textural features including co-occurrence matrices such as grey-tone spatial dependence matrices. In select embodiments, the one or more textural features include maximum, mean, and total imaging signal between the different lesions.

In some embodiments, the features that consider differences in imaging signals across different lesions from the first scan may comprise standard deviation, skewness, kurtosis, and combinations between the different lesions. These values evaluate the distribution (e.g., heterogeneity) of the molecular imaging signal values in the entire subject and/or the integrated value of the molecular imaging signal values in the entire subject.

Processing the first imaging scan comprises calculating uptake values of the molecular imaging agent for each lesion and the disease treatment assessment score comprises evaluation of the uptake values for features directed to individual lesions, for features that consider differences in uptake values across any combination or all lesions in the subject, or a combination thereof. The uptake values may include, but are not limited to, maximum values, largest uptake value in the lesion volume; mean values, average of the uptake values in the lesion; total uptake values; or integral of the uptake values taken over the entire volume of the lesion. In some embodiments, the features directed to individual lesions from the first scan comprise total number of lesions, maximum lesion uptake, mean lesion uptake, total lesion uptake, and combinations thereof in the subject.

In some embodiments, the features that consider differences in uptake values (e.g., standardized update values; SUV) across different lesions from the first scan may comprise standard deviation, skewness, kurtosis, and combinations thereof of maximum lesion uptake, mean lesion uptake and total lesion uptake (e.g., $SUV_{max}$, $SUV_{mean}$, $SUV_{total}$, respectively) between the different lesions.

In some embodiments, the features directed to individual lesions from the first scan may comprise: total number of lesions, maximum lesion uptake (e.g., $SUV_{max}$), average or mean lesion uptake (e.g., $SUV_{mean}$), total lesion uptake (e.g., $SUV_{total}$), and combinations thereof in the subject. In some embodiments, the features directed to individual lesions from the first scan comprise the total number of lesions, maximum lesion uptake (e.g., $SUV_{max}$), and total lesion uptake (e.g., $SUV_{total}$) in the subject.

The methods may further comprise acquiring a second imaging scan of the subject wherein the imaging scan is configured to identify and segment lesions, wherein the first scan and second scan are separated by a period of time. In some embodiments, the methods comprise acquiring a second imaging scan of the subject wherein a molecular imaging agent (e.g., a radioactive tracer or contrast agent) allows segmentation of lesions or targets lesions. In some embodiments, the period of time between the first scan is a set number of days, weeks, or months (e.g., 14 days, 1 month, 6 weeks, and the like). In some embodiments, the period of time is that time during which a subject is undergoing a treatment regimen. For example, the period of time may encompass the time period necessary for a course of chemotherapy or radiation for a cancer patient and the second scan may be used to assess the effectiveness of the treatment regimen.

The second scan is processed similarly to the first scan to identify the locations of the lesions, quantify the lesions, and calculate an imaging signal for at least one imaging feature of each lesion. In addition, each lesion in the second scan may be matched with a corresponding lesion from the first scan and changes in the features of each individual lesion (e.g., change in size, shape, volume, imaging signal) may be determined. Thus, the methods may comprise processing the second scan to determine homologous lesions between the first and second scans and measure a change in each corresponding imaging signal.

Matching allows not simply a comparison of the overall measures for each lesion but allows measurements that involve a voxel by voxel comparison between the volumes of the lesions. For example, a distribution histogram formed of differences between corresponding voxels may be created. A registration process, as part of the matching, may also allow identical regions of interest to be defined on both scans eliminating variations in volume-based measurements caused by slightly different volume determinations.

The matching or aligning of lesions from the first scan to the second scan may be completed by a variety of image analysis tools (See for example, U.S. Pat. No. 9,603,567 and Yip et al. *Phys Med Biol.* 2014, each incorporated herein by reference). In some embodiments, the matching and registration process may mathematically "slide" data of volume of the lesion from the second scan with respect to the lesion of the first scan to measure a correlation between the values of those volumes (e.g., imaging signal or other radiomic imaging feature data). This sliding process may be conducted in multiple dimensions, for example vertically and horizontally, and in multiple dimensions of rotation, including accounting for potential deformations between the scans, until a best match is obtained. The ability to correlate in rotation and deformation allows for matching lesions in limbs and easy deformable tissues to accommodate the bending of limbs or deformation of tissue of the subject between scans. For this purpose, the rotation and deformation may be constrained to reflect possible movement of the particular limb, or tissue plasticity related to the identified anatomical regions and conditioned by mechanical properties of the particular tissue. The matching process may simply select lesions that are closest together in the first and second scan images before or after registration and/or may look at relative size and shape of the lesions. The matching may provide increased accuracy in the methods by monitoring lesion growth, shrinkage, fusion, fission, appearance, disappearance, or migration of one lesion over time or with respect to other identified lesions.

Following matching of lesions, each lesion may be classified based on changes in the features of the lesions from the first scan to its corresponding lesion of the second scan. The features of the lesions used for classification may include those features as described elsewhere herein. See, for example, Perk et al. *Phys Med Biol.* 2018, Kyriakopoulos, C. E., et al., J Clin Oncol, 2020, and Lin, C., et al., *J Nucl Med,* 2016, each of which is incorporated herein by reference. Each lesion, or each lesion location, may be classified based on the features as completely responding (iCR), partially responding (iPR), stable (iSD), progressing (iPD), or new (iNL).

The methods comprise providing a disease treatment assessment score based on evaluation of the imaging signal from the first or second scan for features directed to individual lesions or for features that consider differences in imaging signals across any combination or all lesions in the subject from the second scan, the change in features directed to individual lesions between the first and second scans, the change in features that consider differences in at least one imaging signal across different lesions for homologous lesions between the first and second scans, or a combination thereof.

The change in features directed to individual lesions from the second scan may comprise: changes in total number of lesions, maximum, mean, and total imaging signal between the individual lesions and combinations thereof in the subject. In some embodiments, the change in features that considers differences in imaging signals across different lesions from the second scan comprise: changes in one or more textural features of maximum, mean, and total imaging signal between the different lesions. In some embodiments, the change in features directed to individual lesions from the second scan comprises changes in total number of lesions, max imaging signal ($I_{max}$), mean imaging signal ($I_{mean}$), total imaging signal ($I_{total}$), or combinations thereof in the subject. In some embodiments, the change in features directed to individual lesions from the second scan comprise changes in total number of lesions, maximum, mean, and total uptake values (e.g., $SUV_{max}$, $SUV_{mean}$, $SUV_{total}$), and combinations thereof in the subject.

The change in imaging features that consider differences in Is across different lesions from the second scan may comprise: changes in standard deviations for maximum, mean, total or other imaging signal between the different lesions in a single scan ($\Delta$Hetero $I_{max}$, $\Delta$Hetero $I_{mean}$, and $\Delta$Hetero $I_{total}$, respectively); standard deviations of the change in $I_{max}$, $I_{mean}$, and $I_{total}$ (Hetero $\Delta I_{max}$, Hetero $\Delta I_{mean}$, and Hetero $\Delta I_{total}$, respectively); standard deviations for skewness ($\Delta$Skewness) and kurtosis ($\Delta$Kurtosis) for $I_{max}$, $I_{mean}$, and $I_{total}$; total number of lesions classified as completely responding (iCR), partially responding (iPR), stable (iSD), progressing (iPD), or new (iNL); sum of lesions classified as completely responding (iCR) and partially responding (iPR); proportion of the total number of lesions classified in each of completely responding (iCR), partially responding (iPR), stable (iSD), progressing (iPD), or new (iNL); proportion of the total number of lesions classified as completely responding (iCR) and partially responding (iPR); proportion of the total number of lesions classified as progressing (iPD) and new (iNL); standard deviations of the change in maximum, mean, and total imaging signal for lesions classified as progressing (iPD; Hetero $\Delta$Progressors); standard deviations of the change in $I_{max}$, $I_{mean}$, and $I_{total}$ for lesions classified as partially responding (iPR; Hetero $\Delta$Responders); standard deviations of the $I_{mean}$ from first scan of lesions classified as progressing (iPD) following second scan (Progressors Hetero 1), standard deviations of the $I_{mean}$ of lesions classified as progressing (iPD) and new (iNL) (Progressors Hetero 2), and the percent change between the two ($\Delta$Progressors Hetero); standard deviations of the $I_{mean}$ from first scan of lesions classified as completely responding (iCR) and partially responding (iPR) following second scan (Responders Hetero 1), standard deviations of the $I_{mean}$ of lesions classified as partially responding (iPR) (Responders Hetero 2), and the percent change between the two ($\Delta$Responders Hetero); highest lesion imaging signal (Progressors Max), average lesion imaging signal (Progressors Mean), and total lesion imaging signal (Progressors Total) in the subject of lesions classified as progressing (iPD) from first scan following second scan, highest lesion imaging signal, average lesion imaging signal, and total lesion imaging signal in the subject of lesions from the second scan classified as progressing (iPD) and new (iNL), and the percent change between the two; highest lesion imaging signal (Responders Max), average lesion imaging signal (Responders Mean), and total lesion imaging signal (Responders Total) in the subject of lesions classified as completely responding (iCR) and partially responding (iPR) from first scan following second scan, highest lesion imaging signal, average lesion imaging signal, and total lesion imaging signal in the subject of lesions from the second scan classified as partially responding (iPR), and the percent change between the two; and combinations thereof.

In some embodiments, the change in features that consider differences in imaging signals (I) across different lesions comprise: total number of lesions classified as progressing (iPD) or new (iNL); standard deviations of the change in $I_{max}$, $I_{mean}$, and $I_{total}$ for lesions classified as progressing (iPD); standard deviations of the $I_{mean}$ from first scan of lesions classified as progressing (iPD) following second scan; standard deviations of the $I_{mean}$ of lesions classified as progressing (iPD) and new (iNL); highest lesion imaging signal and total lesion imaging signal in the subject of lesions classified as progressing (iPD) from first scan following second scan; highest lesion imaging signal and total lesion imaging signal in the subject of lesions from the second scan classified as progressing (iPD) and new (iNL); average lesion imaging signal in the subject of lesions from the second scan classified as progressing (iPD) and new (iNL); and combinations thereof.

In some embodiments, the change in imaging features that consider differences across different lesions from the second scan may comprise: changes in standard deviations for maximum, mean, or total imaging agent uptake values (e.g., $SUV_{max}$, $SUV_{mean}$, and $SUV_{total}$) between the different lesions (e.g., $\Delta$Hetero $SUV_{max}$, $\Delta$Hetero $SUV_{mean}$, and $\Delta$Hetero $SUV_{total}$, respectively); standard deviations of the change in maximum, mean, or total imaging agent uptake values (e.g., Hetero $\Delta SUV_{max}$, Hetero $\Delta SUV_{mean}$, and Hetero $\Delta SUV_{total}$, respectively); standard deviations for skewness ($\Delta$Skewness) and kurtosis ($\Delta$Kurtosis) for maximum, mean, or total imaging agent uptake values (e.g., $SUV_{max}$, $SUV_{mean}$, and $SUV_{total}$; total number of lesions classified by a particular imaging metric (e.g., lesion volume) as completely responding (iCR), partially responding (iPR), stable (iSD), progressing (iPD), or new (iNL); sum of lesions classified as completely responding (iCR) and partially responding (iPR); proportion of the total number of lesions classified in each of completely responding (iCR), partially responding (iPR), stable (iSD), progressing (iPD), or new (iNL); proportion of the total number of lesions classified as completely responding (iCR) and partially responding (iPR); proportion of the total number of lesions classified as progressing (iPD) and new (iNL); standard deviations of the change in maximum, mean, or total uptake values (e.g., $SUV_{max}$, $SUV_{mean}$, and $SUV_{total}$) for lesions classified as progressing (iPD) (Hetero $\Delta$Progressors); standard deviations of the change in maximum, mean, or total uptake values (e.g., $SUV_{max}$, $SUV_{mean}$, and $SUV_{total}$) for lesions classified as partially responding (iPR) (Hetero $\Delta$Responders); standard deviations of mean uptake values (e.g., $SUV_{mean}$) from first scan of lesions classified as progressing (iPD) following second scan (Progressors Hetero 1), standard deviations of mean uptake values (e.g., $SUV_{mean}$) of lesions classified as progressing (iPD) and new (iNL) (Progressors Hetero 2), and the percent change between the two ($\Delta$Progressors Hetero); standard deviations of mean uptake values (e.g., $SUV_{mean}$) from first scan of lesions classified as completely responding (iCR) and partially responding (iPR) following second scan (Responders Hetero 1), standard deviations of mean uptake values (e.g., $SUV_{mean}$) of lesions classified as partially responding (iPR) (Responders Hetero 2), and the percent change between the two ($\Delta$Responders Hetero); highest lesion uptake imaging signal (Progressors Max), average lesion uptake (Progressors Mean), and total lesion uptake (Progressors Total) in the subject of lesions classified as progressing (iPD) from first scan following second scan, highest lesion uptake, average lesion uptake, and total lesion uptake in the subject of lesions from the second scan classified as progressing (iPD) and new (iNL), and the percent change between the two; highest lesion uptake (Responders Max), average lesion uptake (Responders Mean), and total lesion uptake (Responders Total) in the subject of lesions classified as completely responding (iCR) and partially responding (iPR) from first scan following second scan, highest lesion uptake, average lesion uptake, and total lesion uptake in the subject of lesions from the second scan classified as partially responding (iPR), and the percent change between the two; and combinations thereof.

In some embodiments, the change in features that consider differences in uptake values (e.g., SUVs) across different lesions comprise: total number of lesions classified as progressing (iPD) or new (iNL); standard deviations of the change in maximum, mean, or total uptake values (e.g., $SUV_{max}$, $SUV_{mean}$, and $SUV_{total}$) for lesions classified as progressing (iPD); standard deviations of mean uptake values (e.g., $SUV_{mean}$) from first scan of lesions classified as progressing (iPD) following second scan; standard deviations of mean uptake values (e.g., $SUV_{mean}$) of lesions classified as progressing (iPD) and new (iNL); highest lesion uptake and total lesion uptake in the subject of lesions classified as progressing (iPD) from first scan following second scan; highest lesion uptake and total lesion uptake in the subject of lesions from the second scan classified as progressing (iPD) and new (iNL); average lesion uptake in the subject of lesions from the second scan classified as progressing (iPD) and new (iNL); and combinations thereof.

The methods may comprise acquiring any number of additional scans of the subject at a later time and repeating any or all of the above methods steps. In such instances, the disease assessment score may evaluate the progression or regression of the disease over time or after different treatment regimens. Thus, the methods may allow short- or long-term longitudinal evaluation of single or multiple treatment regimens.

Thus, the methods may further comprise acquiring at least one additional imaging scan of the subject wherein the imaging scan is configured to identify and segment lesions; and processing the at least one additional imaging scan to: identify locations of the lesions, quantify the lesions in the subject, and calculate an imaging signal for at least one imaging feature of each lesion; determine homologous lesions between any two imaging scans and measure a change in each corresponding imaging signal, classify each lesion based on the change in each lesion; providing a disease treatment assessment score based on evaluation of the imaging signal directed to individual lesions or for features that consider differences in imaging signals across any combination or all lesions in the subject from the at least one additional imaging scan, the change in features directed to individual lesions between any two imaging scans, the change in features that consider differences in at least one imaging signal across different lesions for homologous lesions between any two imaging scans, or a combination thereof. Descriptions of the acquiring, processing, and providing steps as provided elsewhere herein in regards to the first scan and the second scan are applicable to the at least one additional imaging scan.

The methods may further comprise acquiring an anatomical scan (e.g., CT, MRI, ultrasound). For example, an anatomical scan may be acquired at the same time as the first scan, at the same time as the second scan, or at the same time as both the first and second scan. The anatomical scan may help match corresponding lesions due to relationships between known anatomical locations. The anatomical locations may also assist in the identification of lesions and removal of tissues or other anatomical features when determining lesions measurements and imaging signal values. The methods may include processing the anatomical scan and producing a set of anatomical regions of interest.

In some embodiments, the methods further comprise classifying the lesions according to anatomical location (e.g., in a particular type of tissue (e.g., breast or bone) or segment of the body (e.g., leg or brain). The methods may provide feature measurements for subsets of lesions based on anatomical location. Thus, the methods may provide information on groups of lesions. In some embodiments, the disease treatment assessment score is further based on evaluation of anatomical locations of lesions, anatomical distribution of lesions, or a combination thereof.

In some embodiments, the features may be radiomic features. Radiomic features can be divided into various groups, such as size and shape based-features, descriptors of the image intensity histogram, descriptors of the relationships between image voxels (e.g., gray-level co-occurrence matrix (GLCM), run length matrix (RLM), size zone matrix (SZM), and neighborhood gray tone difference matrix (NGTDM) derived textures), textures extracted from filtered images, and fractal features. The mathematical definitions of these features are independent of imaging modality and are known in the art. In some embodiments, the disease treatment assessment score is further based on radiomics features.

The disease treatment assessment score may be further based on other non-imaging data. For example, the disease treatment assessment score may incorporate results from biomarkers (e.g., prostate-specific antigen (PSA), circulating tumor cells (CTCs), circulating tumor DNA (ctDNA), and other biomarkers). In some embodiments, the biomarkers may be indicative of a disease (e.g., disease-related biomarkers) or general patient health (e.g., genomic, proteomic, metabolomic data).

Figure 6:
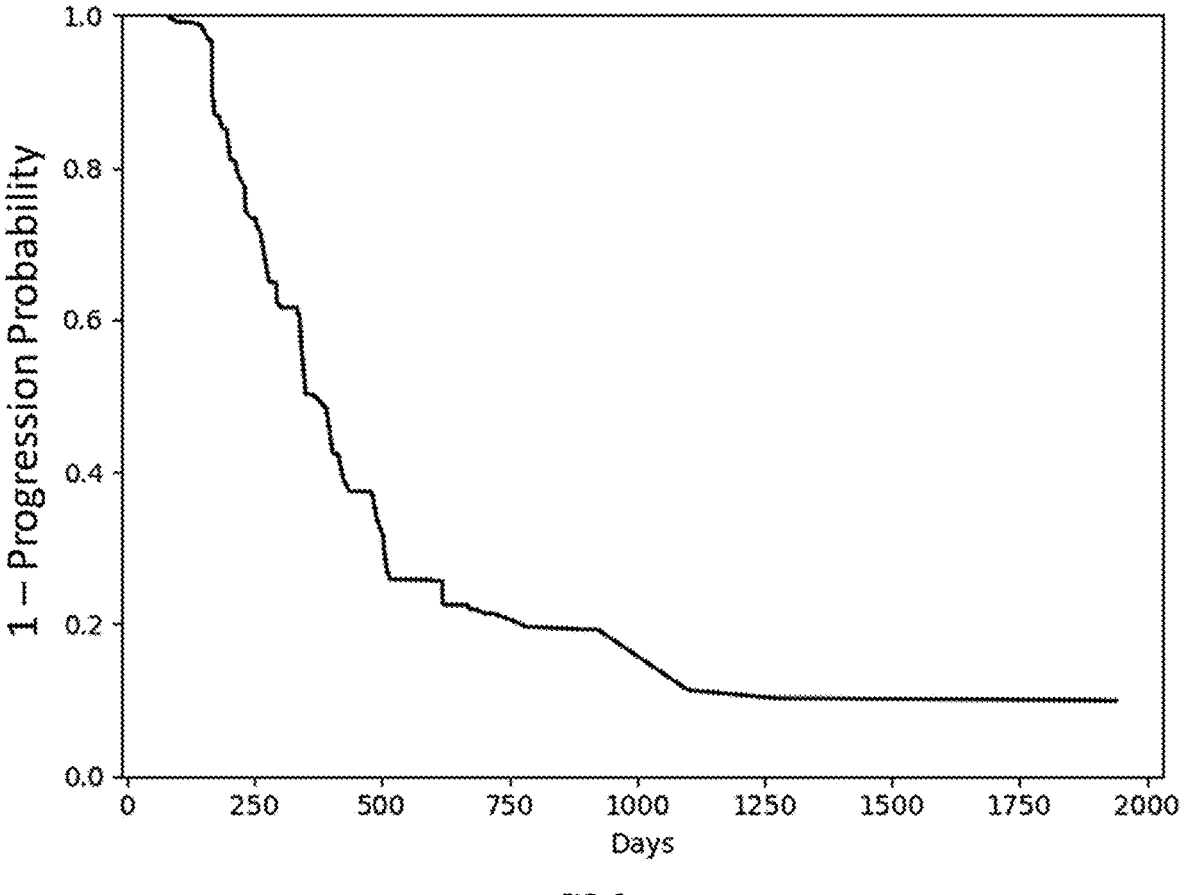
FIG. 6 shows an example output of the machine learning model. The graph plots likelihood a patient will have progressed vs time.

The methods may further comprise providing a disease projection analysis based on simulation of disease treatment. In some embodiments, the disease projection analysis may remove a specific lesion or combinations thereof from a previous imaging scan to monitor simulation disease progression. In some embodiments, the disease projection analysis may change one or more imaging features from a previous imaging scan to be representative of successful treatment of a specific lesion (e.g., decrease in size or total uptake of imaging agent) or combinations thereof to monitor simulation disease progression. In some embodiments, the disease projection analysis comprises a simulated survival curve, as shown in FIG. 6.

The present disclosure also provides non-transitory computer-readable media. The non-transitory computer-readable media stores instructions that when executed by one or more processors performs some or all of the operations described in the disclosed methods.

In some embodiments, the one or more processors perform operations comprising at least one or all of: receiving a first imaging scan of a subject and related scan and subject demographics, wherein the imaging scan is configured to identify and segment lesions in the subject; processing the first imaging scan to identify locations of the lesions, quantify the total number of lesions, and determine features for each lesion (e.g., imaging signal values, e.g., uptake values of an imaging agent); evaluating the features directed to individual lesions, the features that consider differences in imaging signal values, e.g., uptake values, across any combination or all lesions in the subject, or a combination thereof; and providing a disease treatment assessment score. Scan and subject demographics may include at least one of date and time of the scan, molecular imaging agent used in the scan, type of scan and/or type of scanner, description of scan (e.g., locations, depth, etc.), description of subject diagnosis or suspected disease, description of subject (e.g., gender, height, age, weight) or any additional information regarding the subject which may assist in carrying out the disclosed methods (e.g., amputations, removed organs or organ damage, and the like).

The processors may further perform any or all of the operations of: receiving a second imaging scan of a subject and related scan and subject demographics, wherein the imaging scan is configured to identify and segment lesions; processing the second imaging scan to identify locations of the lesions, quantify the total number of lesions, and determine features for each lesion (e.g., imaging signal values, e.g., uptake values of an imaging agent); determining homologous lesion location between the first and second scans; receiving at least one additional imaging scan and related scan and subject demographics, wherein the at least one imaging scan is configured to identify and segment lesions; processing the at least one additional imaging scan to identify locations of the lesions, quantify the total number of lesions, and calculate an imaging signal for at least one imaging feature of each lesion; determining homologous lesion location between any two imaging scans; measuring a change in any or all of the corresponding imaging signals;

receiving an anatomical scan concomitantly with the first imaging scan, the second imaging scan, or both; classifying the lesions from the first imaging scan, the second imaging scan or both according to anatomical location; evaluating individual lesions in a subset of anatomical locations of the subject, for features that consider differences across lesions within a subset of anatomical locations of the subject or between different subsets of anatomical locations of the subject; receiving a radiometric scan; extracting radiomic features from any or all of the radiometric scans; evaluating changes in at least one radiomic feature to classify lesions as progressing or responding; and receiving disease-related biomarker data; or a combination thereof.

The methods described herein can be implemented as a system including one or more processors and a computer-readable medium storing instructions executable by the one or more processors to perform operations, as described above. The system may comprise at least one computer system comprising the one or more processors and/or the computer-readable media. The system may further comprise one or more local servers or databases connected to or integrated with the one or more computer system. The one or more processors may be configured to communicate via wired or wireless communications with each other or other processors. The one or more processors may be configured to operate on one or more processor-controlled devices that can be similar or different devices.

The systems, methods and readable media described herein protect the confidentiality and security of protected health information (PHI) in compliance with various privacy standards (e.g., Health Insurance Portability and Accountability Act (HIPAA)). Thus, the systems, methods and readable media may be considered HIPAA-compliant. The systems, methods and readable media may provide or allow one or all of: means of access control, mechanisms to authenticate electronic PHI, functionalities for encryption/decryption, and mechanisms to log activity and implement audits. Data may be communicated using known encryption/decryption and security techniques. For example, DICOM imaging standards support encryption. The system and methods may anonymize any protected subject data.

In some embodiments, the system displays to a user one or more of: a) a risk score, b) scan images, c) treatment recommendations, or the like.

In some embodiments, data is collected at a first location (e.g., a scanning center) and transferred to a second location for analysis. In some embodiments, analyzed data or reports are transferred back to or otherwise made available to the first location or to a third location (e.g., a location of treating physician or a location of a patient).

In some embodiments, the methods described herein are integrated into a treatment method for a subject. For example, in some embodiments, a subject undergoes one or more scans, data is analyzed by the systems and methods described herein, a report of the results is generated, and the subject is treated based on the results (e.g., continued existing treatment, change in treatment (e.g., change in intervention type, dose, timing, etc.), watchful waiting, etc.).

Examples

Methods

Patient Population Patients from three independent clinical trials of prostate cancer patients were gathered and assessed retrospectively. Each trial consisted of prostate cancer patients imaged with $^{18}$F-NaF PET/CT imaging at baseline and after 2 or 3 months. A breakdown of the patients included is shown in Table 1.

TABLE 1

| | | Clinical trials | | |
|---|---|---|---|---|
| Dataset | | PCF | NCI | MVI |
| Clinical Trial Number | | Trial 1 | Trial 3 | Trial 4 |
| Primary Objective | | To determine the repeatability of NaF PET/CT imaging for evaluating osseous metastases in patients with metastatic castrate-resistant prostate cancer (test-retest study). | Determine if PSA-TRICOM combined with enzalutamide will increase time to progression in chemotherapy-naive metastatic castration resistant prostate cancer patients compared to enzalutamide alone. | To evaluate the 2-year metastasis-free survival of patients with non-metastatic prostate cancer (clinical stage D0) treated with a DNA vaccine encoding PAP, with GM-CSF as an adjuvant, versus patients treated with GM-CSF only. |
| Imaging Timepoints | | Baseline, end-of-cycle 3 (2 or 3 months) | Baseline, 2 or 3 months | Baseline, 3 months |
| Patients | | 56 (44 multiple timepoints) | 18 | 34 |
| Disease | | mCRPC | mCRPC | mCSPC |
| Treatments | | Docetaxel, Docetaxel + Abirarterone, Abiraterone, Enzalutimide, Orteronel, or Abiraterone + Veliparaib | Enzalutamide or Enza + PSA-TRICOM Vaccine | GM-CSF or GM-CSF + pTVG-HP Vaccine |
| Scanner | | GE Discovery VCT (UW and MSK) Phillips Gemini TF (NCI) | Philips Gemini TF TOF Siemens Biograph mCT | GE Discovery RX (JHU) GE Discovery 710 (UW) |

Image Processing Images were processed using the ΔIQ Solutions bone metastases application. Statistically optimized regional thresholds were used to identify candidate lesions as in Perk, T. G., et al., Physics in Medicine and Biology, 2018. 63(22): p. 1-10. and a patient specific adaption factor was applied to patients with elevated background bone uptake. A previously trained and tested random forest model was used to remove benign lesions from analysis (See, Perk, T. G., et al., Physics in Medicine and Biology, 2018. 63(22): p. 1-12). As the PCF dataset was used to train the random forest model, leave-one-out cross validation was used to classify lesions in that dataset. For each lesion quantitative metrics were extracted: such as the highest uptake within the lesion ($SUV_{max}$), average lesion uptake ($SUV_{mean}$), active tumor burden ($SUV_{total}=SUV_{mean}\times$Tumor Volume, TLG-equivalent for NaF PET), and $SUV_{peak}$ (Average SUV of a 1 $cm^3$ around the highest uptake voxel of the lesion).

Articulated registration was used to track matching lesions across timepoints. Lesions were classified into response categories based on test-retest limits of agreement for $SUV_{total}$, adjusted based on lesion size (Table 2). The 5 response categories are: complete response (CR, a lesion on baseline had no matched lesion on follow-up), partial response (PR, change in $SUV_{total}$<lower test-retest limit), stable disease (SD, $SUV_{total}$ between test-retest limits), progressive disease (PD, change in $SUV_{total}$>upper test-retest limit), and new lesion (NL, a lesion on follow-up that had no matched lesion on baseline).

TABLE 2

Test-retest limits of agreement for the relative change in lesion $SUV_{total}$ from a previous study. Limits were widened for lesions smaller than 1.5 $cm^3$

| Metric | Size > 1.5 $cm^3$ | Size < 1.5 $cm^3$ |
| --- | --- | --- |
| $SUV_{total}$ | −37%, +71% | −68%, +250% |

Implementation of Previously Reported Models Two methods for patient-level classification identified from literature were implemented to the four patient populations available. Specifically, Harmon et al. (J Clin Oncol, 2017. 35(24): p. 2829-2837) demonstrated that patients could be separated into having progressive, stable, or responding disease based on changes in $SUV_{total}$ after three cycles of treatment, which showed strong correlations to both radiographic and clinical progression free survival (PFS). The limits from Lin et al. (J Nucl Med, 2016. 57(12): p. 1872-1879) were used to classify patients as having progressive disease ($\Delta SUV_{total}$>44%), stable disease (−30%<$\Delta SUV_{total}$<44%), or partial response ($\Delta SUV_{total}$<−30%). The implementation was slightly different in that a single threshold of SUV >15 g/ml and manual physician classification were used and herein SORT thresholds and random forest-based lesion classification were used.

Recently, a NaF version of the PERCIST (PET Response Criteria in Solid Tumors) criteria was proposed (NAFCIST: $Na^{18}F$ PET response criteria in primary bone tumours) (See, Kairemo, K., et al., ESMO Open, 2019. 4(1): p. e000439). Similar to the PERCIST criteria, NAFCIST measures $SUV_{peak}$ of the highest-uptake lesion each of subsequent scans. The secondary criteria involve changes in $SUV_{total}$ of the five highest uptake lesions (no more than 2 per organ) or the new lesions at the secondary timepoint. Patients are classified as partial responders if $SUV_{peak}$ of the hottest lesion decreased by over 30% and patients are classified as progressive if there was an increase in SUVpeak of the hottest lesion >30%, an $SUV_{total}$ increase of the two hottest lesions >75%, or any new lesions. Patients that did not meet either criteria were classified as stable disease. This methodology was previously implemented manually, in this work it was implemented automatically. A third method used changes in PSA levels between baseline and follow-up (See, Rescign, P., et al., JCO, 2018, 36(15_suppl) 5063-5063).

AIQ Analysis For each patient, 84 imaging features were extracted, with a full list of features shown in Table 2. The features are separated into categories based on whether they are measured at a single timepoint (baseline or follow-up) or capture response (change from baseline to follow-up). In addition, features were considered to either describe homogeneity or heterogeneity. A homogeneity feature describes a feature that does not consider differences in uptake across lesions within a patient, such as the maximum lesion uptake and the average lesion uptake. In contrast, heterogeneity features reflect the differences across lesions. Heterogeneity features included the standard deviation, skewness, and kurtosis of lesion uptake, as well as the proportion of lesions in each response lesion category. Lesions that were classified as PR or PD were assessed together to determine the maximum, mean, total, and standard deviation of mean (hetero) for just each category and then determine the changes of within those lesion populations for the patient. With respect to response of standard deviations (hetero) of lesion values, this was computed in two ways, the change in standard deviations (ΔHetero) or the standard deviation of lesion changes (Hetero Δ).

TABLE 3

Imaging metrics extracted from each patient image. Metrics are divided into baseline, follow-up, or response, as well as homogeneity (whole patient summary) or heterogeneity (individual lesion driven).

| Class | Baseline | Follow-Up | Response |
| --- | --- | --- | --- |
| Homogeneity | $N_{lesions}$ | $N_{lesions}$ | $\Delta N_{lesions}$ |
| | Patient total imaging signal | Patient total imaging signal | ΔPatient total imaging signal |
| | Patient maximum imaging signal | Patient maximum imaging signal | ΔPatient maximum imaging signal |
| | Patient $SUV_{mean}$ | Patient $SUV_{mean}$ | ΔPatient $SUV_{mean}$ |
| Heterogeneity | Hetero $SUV_{total}$ | Hetero $SUV_{total}$ | ΔHetero $SUV_{total}$    Hetero $ASUV_{total}$ |
| | Hetero $SUV_{max}$ | Hetero $SUV_{max}$ | ΔHetero $SUV_{max}$    Hetero $ASUV_{max}$ |
| | Hetero $SUV_{mean}$ | Hetero $SUV_{mean}$ | ΔHetero $SUV_{mean}$    Hetero $ASUV_{mean}$ |
| | Skewness $SUV_{total}$ | Skewness $SUV_{total}$ | ΔSkewness $SUV_{total}$ |
| | Skewness $SUV_{max}$ | Skewness $SUV_{max}$ | ΔSkewness $SUV_{max}$ |
| | Skewness $SUV_{mean}$ | Skewness $SUV_{mean}$ | ΔSkewness $SUV_{mean}$ |

TABLE 3-continued

Imaging metrics extracted from each patient image. Metrics are divided into baseline, follow-up, or response, as well as homogeneity (whole patient summary) or heterogeneity (individual lesion driven).

| Class | Baseline | Follow-Up | Response | |
|---|---|---|---|---|
| | Kurtosis $SUV_{total}$ | Kurtosis $SUV_{total}$ | $\Delta$Kurtosis $SUV_{total}$ | |
| | Kurtosis $SUV_{max}$ | Kurtosis $SUV_{max}$ | $\Delta$Kurtosis $SUV_{max}$ | |
| | Kurtosis $SUV_{mean}$ | Kurtosis $SUV_{mean}$ | $\Delta$Kurtosis $SUV_{mean}$ | |
| | | | $N_{CR}$ | $N_{CR}$/N |
| | | | $N_{SD}$ | $N_{SD}$/N |
| | | | $N_{PR}$ | $N_{PR}$/N |
| | | | $N_{PD}$ | $N_{PD}$/N |
| | | | $N_{NL}$ | $N_{NL}$/N |
| | | | $N_{CR+PR}$/N | $N_{NL+PD}$/N |
| | | | Hetero $\Delta$Responders Total | Hetero $\Delta$Progressors Total |
| | | | Hetero $\Delta$Responders Max | Hetero $\Delta$Progressors Max |
| | | | Hetero $\Delta$Responders Mean | Hetero $\Delta$Progressors Mean |
| | | | Progressors Hetero 1 | Responders Hetero 1 |
| | | | Progressors Hetero 2 | Responders Hetero 2 |
| | | | $\Delta$Progressors Hetero | $\Delta$Responders Hetero |
| | | | Progressors Max 1 | Responders Max 1 |
| | | | Progressors Max 2 | Responders Max 2 |
| | | | $\Delta$Progressors Max | $\Delta$Responders Max |
| | | | Progressors Mean 1 | Responders Mean 1 |
| | | | Progressors Mean 2 | Responders Mean 2 |
| | | | $\Delta$Progressors Mean | $\Delta$Responders Mean |
| | | | Progressors Total 1 | Responders Total 1 |
| | | | Progressors Total 2 | Responders Total 2 |
| | | | $\Delta$Progressors Total | $\Delta$Responders Total |

To assess the ability of these features to predict clinical benefit, a random survival forest (RSF) model was implemented separately in each dataset. To do this, two separate training and testing cases were performed. First, the PCF data was selected for model training, as it had the most patients (44 patients), varied treatment types (6 treatments), and was acquired from 3 imaging centers. In the second approach, the data from the other two datasets were used to create a second model that was tested on the PCF data. In each approach, the training data was used to train 6 different sets of RSF models: all features, baseline, follow-up, response, homogeneity, and heterogeneity. After training, the weights of each model were locked and applied to the testing data. Patients that only received baseline or follow-up imaging were included in models where appropriate. Patients that were taken off of treatment before follow-up imaging were only included in the baseline models. Random survival forests were implemented in Python using scikit-survival.

Statistical Analysis For each patient in all datasets, the duration of clinical benefit was defined as the number of days from the beginning of treatment to the day the patient was taken off treatment due to any factor, such as event of disease progression (radiographic, biochemical, or clinical) or death, whichever came first.

For each dataset, univariate Cox-proportional hazards regression was performed on each metric. Three separate models were assessed for their ability to predict clinical benefit in each dataset, each of which is outlined below. The performance of the models was compared using the concordance index (C-index). The significance of the c-index was determined using a permutation test that tested that the c-index would not result from random chance. To do this, the duration of clinical benefit and censorship were randomly shuffled 1000 times and the c-index was recalculated for each permutation. The percentage of incidents where the c-index was greater than the model c-index was taken as the p-value.

Kaplan-Meier analysis was used to assess the patient classification methods of the Harmon et al., NAFCIST, and PSA changes. As an illustration of the separation robustness of the RSF models, the median risk score of the training data was used to separate the testing data into above and below the median risk score. Significance of Kaplan-Meier analysis was determined using the log-rank test to compare the groups.

All reported P values are two-sided, and $P<0.05$ was used to define statistical significance. Analysis was performed in Python.

The below equations define the relationships used herein, where $N_{lesions}$ is the number of lesions, NCR is the number of complete responding lesions (CR), $N_{SD}$ is the number of stable disease lesions based on change in total imaging signal (SD), $N_{PR}$ is the number of partial responding lesions based on change in total imaging signal (PR), $N_{PD}$ is the number of progressive disease lesions based on change in total imaging signal (PD) and $N_{NL}$ is the number of new lesions (NL).

$$\text{Patient } SUV_{total} \sum_{all\ lesions} SUV_{total,lesion} \tag{1}$$

$$\text{Patient } SUV_{max} \max_{all\ lesions} (SUV_{max,lesion}) \tag{2}$$

$$\text{Patient } SUV_{mean} \frac{\sum_{all\ lesions} SUV_{total,lesion}}{N_{lesions}} \tag{3}$$

$$\text{Hetero } SUV_{total} \sqrt{\frac{\sum_{all\ lesions} (SUV_{total,lesion} - \text{average } SUV_{total})^2}{N_{lesions}}} \tag{4}$$

-continued $$Hetero\ SUV_{max} \sqrt{\frac{\sum_{all\ lesions}(SUV_{max,lesion} - \text{average } SUV_{max})^2}{N_{lesions}}} \quad (5)$$

$$Hetero\ SUV_{mean} \sqrt{\frac{\sum_{all\ lesions}(SUV_{max,lesion} - \text{average } SUV_{mean})^2}{N_{lesions}}} \quad (6)$$

$$Skewness\ SUV_{total} \frac{\frac{1}{N_{lesions}}\sum_{all\ lesions}(SUV_{total,lesion} - \text{average } SUV_{total})^3}{\left(\sqrt{\frac{1}{N_{lesions}}\sum_{all\ lesions}(SUV_{total,lesion} - \text{average } SUV_{total})^2}\right)^3} \quad (7)$$

$$Skewness\ SUV_{max} \frac{\frac{1}{N_{lesions}}\sum_{all\ lesions}(SUV_{max,lesion} - \text{average } SUV_{max})^3}{\left(\sqrt{\frac{1}{N_{lesions}}\sum_{all\ lesions}(SUV_{max,lesion} - \text{average } SUV_{max})^2}\right)^3} \quad (8)$$

$$Skewness\ SUV_{mean} \frac{\frac{1}{N_{lesions}}\sum_{all\ lesions}(SUV_{mean,lesion} - \text{average } SUV_{mean})^3}{\left(\sqrt{\frac{1}{N_{lesions}}\sum_{all\ lesions}(SUV_{mean,lesion} - \text{average } SUV_{mean})^2}\right)^3} \quad (9)$$

$$Kurtosis\ SUV_{total} \frac{\frac{1}{N_{lesions}}\sum_{all\ lesions}(SUV_{total,lesion} - \text{average } SUV_{total})^4}{\left(\frac{1}{N_{lesions}}\sum_{all\ lesions}(SUV_{total,lesion} - \text{average } SUV_{total})^2\right)^2} \quad (10)$$

$$Kurtosis\ SUV_{max} \frac{\frac{1}{N_{lesions}}\sum_{all\ lesions}(SUV_{max,lesion} - \text{average } SUV_{max})^4}{\left(\frac{1}{N_{lesions}}\sum_{all\ lesions}(SUV_{max,lesion} - \text{average } SUV_{max})^2\right)^2} \quad (11)$$

$$Kurtosis\ SUV_{mean} \frac{\frac{1}{N_{lesions}}\sum_{all\ lesions}(SUV_{mean,lesion} - \text{average } SUV_{mean})^4}{\left(\frac{1}{N_{lesions}}\sum_{all\ lesions}(SUV_{mean,lesion} - \text{average } SUV_{mean})^2\right)^2} \quad (12)$$

$$\Delta metric\ \frac{metric\ 2 - metric\ 1}{metric\ 1} * 100 \quad (13)$$

$$\Delta Hetero\ SUV_{total}\ \frac{Hetero\ SUV_{total}2 - Hetero\ SUV_{total}1}{Hetero\ SUV_{total}1} * 100 \quad (14)$$

$$\Delta Hetero\ SUV_{max}\ \frac{Hetero\ SUV_{max}2 - Hetero\ SUV_{max}1}{Hetero\ SUV_{max}1} * 100 \quad (15)$$

$$\Delta Hetero\ SUV_{mean}\ \frac{Hetero\ SUV_{mean}2 - Hetero\ SUV_{mean}1}{Hetero\ SUV_{mean}1} * 100 \quad (16)$$

$$Hetero\ \Delta SUV_{total} \sqrt{\frac{\sum_{matched\ lesions}(\Delta SUV_{total,lesion} - \text{average } \Delta SUV_{total})^2}{N_{matched\ lesions}}} \quad (17)$$

$$Hetero\ \Delta SUV_{max} \sqrt{\frac{\sum_{matched\ lesions}(\Delta SUV_{max,lesion} - \text{average } \Delta SUV_{max})^2}{N_{matched\ lesions}}} \quad (18)$$

$$Hetero\ \Delta SUV_{mean} \sqrt{\frac{\sum_{matched\ lesions}(\Delta SUV_{mean,lesion} - \text{average } \Delta SUV_{mean})^2}{N_{matched\ lesions}}} \quad (19)$$

$$N_{CR+PR}/N \frac{N_{CR} + N_{PR}}{N_{CR} + N_{PR} + N_{SD} + N_{PD} + N_{NL}} \quad (20)$$

$$N_{CR}/N \frac{N_{CR}}{N_{CR} + N_{PR} + N_{SD} + N_{PD} + N_{NL}} \quad (21)$$

$$N_{SD}/N \frac{N_{SD}}{N_{CR} + N_{PR} + N_{SD} + N_{PD} + N_{NL}} \quad (22)$$

$$N_{PR}/N \frac{N_{PR}}{N_{CR} + N_{PR} + N_{SD} + N_{PD} + N_{NL}} \quad (23)$$

$$N_{PD}/N \frac{N_{PD}}{N_{CR} + N_{PR} + N_{SD} + N_{PD} + N_{NL}} \quad (24)$$

$$N_{NL}/N \frac{N_{NL}}{N_{CR} + N_{PR} + N_{SD} + N_{PD} + N_{NL}} \quad (25)$$

$$N_{NL+PD}/N \frac{N_{NL} + N_{PD}}{N_{CR} + N_{PR} + N_{SD} + N_{PD} + N_{NL}} \quad (26)$$

$$Hetero\ \Delta Progressors\ Total \sqrt{\frac{\sum_{PD}(\Delta SUV_{total,lesion} - \text{average } \Delta SUV_{total})^2}{N_{PD}}} \quad (27)$$

$$Hetero\ \Delta Progressors\ Max \sqrt{\frac{\sum_{PD}(\Delta SUV_{max,lesion} - \text{average } \Delta SUV_{max})^2}{N_{PD}}} \quad (28)$$

$$Hetero\ \Delta Progressors\ Mean \sqrt{\frac{\sum_{PD}(\Delta SUV_{mean,lesion} - \text{average } \Delta SUV_{mean})^2}{N_{PD}}} \quad (29)$$

$$Progressors\ Hetero\ 1 \sqrt{\frac{\sum_{PD\ at\ time\ 1}(SUV_{mean,lesion} - \text{average } SUV_{mean})^2}{N_{PD}}} \quad (30)$$

$$Progressors\ Hetero\ 2 \sqrt{\frac{\sum_{NL\ and\ PD\ at\ time\ 2}(SUV_{mean,lesion} - \text{average } SUV_{mean})^2}{N_{NL} + N_{PD}}} \quad (31)$$

$$\Delta Progressors\ Hetero\ \frac{Progressors\ Hetero\ 2 - Progressors\ Hetero\ 1}{Progressors\ Hetero\ 1} * 100 \quad (32)$$

$$Progressors\ Max\ 1\ \max_{PD\ at\ time\ 1}(SUV_{max,lesions}) \quad (33)$$

$$Progressors\ Max\ 2\ \max_{NL\ and\ PD\ at\ time\ 2}(SUV_{max,lesions}) \quad (34)$$

$$\Delta Progressors\ Max\ \frac{Progressors\ Max\ 2 - Progressors\ Max\ 1}{Progressors\ Max\ 1} * 100 \quad (35)$$

$$Progressors\ Mean\ 1\ \frac{\sum_{PD\ at\ time\ 1} SUV_{mean,lestion}}{N_{PD}} \quad (36)$$

$$Progressors\ Mean\ 2\ \frac{\sum_{ND\ and\ PD\ at\ time\ 2} SUV_{mean,lesion}}{N_{NL} + N_{PD}} \quad (37)$$

$$\Delta Progressors\ Mean\ \frac{Progressors\ Mean\ 2 - Progressors\ Mean\ 1}{Progressors\ Mean\ 1} * 100 \quad (38)$$

$$Progressors\ Total\ 1\ \sum_{PD\ at\ time\ 1} SUV_{total,lesions} \quad (39)$$

$$Progressors\ Total\ 2\ \sum_{NL\ and\ PD\ at\ time\ 2} SUV_{total,lesions} \quad (40)$$

$$\Delta Progressors\ Total\ \frac{Progressors\ Total\ 2 - Progressors\ Total\ 1}{Progressors\ Total\ 1} * 100 \quad (41)$$

$$Hetero\ \Delta Responders\ Total \sqrt{\frac{\sum_{PR}(\Delta SUV_{total,lesion} - \text{average } \Delta SUV_{total})^2}{N_{PR}}} \quad (42)$$

25

-continued $$\text{Hetero } \Delta Responders \text{ Max} = \sqrt{\frac{\Sigma_{PR}(\Delta SUV_{max,lesion} - \text{average } \Delta SUV_{max})^2}{N_{PR}}} \quad (43)$$

$$\text{Hetero } \Delta Responders \text{ Mean} = \sqrt{\frac{\Sigma_{PR}(\Delta SUV_{mean,lesion} - \text{average } \Delta SUV_{mean})^2}{N_{PR}}} \quad (44)$$

$$Responders \text{ Hetero } 1 = \sqrt{\frac{\Sigma_{CR \text{ and } PR \text{ at time } 1}(SUV_{mean,lesion} - \text{average } \Delta SUV_{mean})^2}{N_{CR} + N_{PR}}} \quad (45)$$

$$Responders \text{ Hetero } 2 = \sqrt{\frac{\Sigma_{PR \text{ at time } 2}(SUV_{mean,lesion} - \text{average } \Delta SUV_{mean})^2}{N_{PR}}} \quad (46)$$

$$\Delta Responders \text{ Hetero} = \frac{Responders \text{ Hetero } 2 - Responders \text{ Hetero } 1}{Responders \text{ Hetero } 1} * 100 \quad (47)$$

$$Responders \text{ Max } 1 = \max_{CR \text{ and } PR \text{ at time } 1}(SUV_{max, \text{ lesions}}) \quad (48)$$

$$Responders \text{ Max } 2 = \max_{PR \text{ at time } 2}(SUV_{max, \text{ lesions}}) \quad (49)$$

$$\Delta Responders \text{ Max} = \frac{Responders \text{ Max } 2 - Responders \text{ Max } 1}{Responders \text{ Max } 1} * 100 \quad (50)$$

$$Responders \text{ Mean } 1 = \frac{\sum_{CR \text{ and } PR \text{ at time } 1} SUV_{mean, \text{ lesion}}}{N_{CR} + N_{PR}} \quad (51)$$

$$Responders \text{ Mean } 2 = \frac{\sum_{PR \text{ at time } 2} SUV_{mean, \text{ lesion}}}{N_{PR}} \quad (52)$$

$$\Delta Responders \text{ Mean} = \frac{Responders \text{ Mean } 2 - Responders \text{ Mean } 1}{Responders \text{ Mean } 1} * 100 \quad (53)$$

$$Responders \text{ Total } 1 = \sum_{PR \text{ at time } 1} SUV_{total, \text{ lesions}} \quad (54)$$

$$Responders \text{ Total } 2 = \sum_{CR \text{ and } PR \text{ at time } 2} SUV_{total, \text{ lesions}} \quad (55)$$

$$\Delta Responders \text{ Total} = \frac{Responders \text{ Total } 2 - Responders \text{ Total } 1}{Responders \text{ Total } 1} * 100 \quad (56)$$

A summary of the number of lesions, duration of benefit, and percent of patient with heterogenous response (having at least one progressing and responding lesion at the same time) of each study is shown in Table 4. The PCF data had the most lesions and shortest benefit while the MVI data had very few lesions. The NCI dataset was somewhere in between. 66 of the 96 patients with multiple PET images exhibited heterogeneous response. This was more prevalent in the patients with larger numbers of lesions.

26

TABLE 4

Median and ranges of baseline number of lesions and duration of benefit for each dataset as well as the percent of patients with both favorable and non-favorable responding lesions.

|  | PCF | NCI | MVI |
|---|---|---|---|
| Number of Lesions | 34 [0-208] | 8 [2-120] | 8 [0-25] |
| Benefit | 224 [2-923] | 716 [168-1939] | 504 [161-685] |
| Heterogeneity | 89% | 67% | 47% |

Correlation of all NaF PET/CT metrics to duration of benefit using Cox-Proportional Hazards regression is shown in Table 5. The hazards ratios for each metric are shown in Table 6. Only the number of progressing lesions had a c-index over 0.6 in all four trials.

TABLE 5

Univariate C-index of imaging metrics for each clinical trial obtained from Cox-Proportional Hazards regression

| Categories | Feature | C-index | | |
|---|---|---|---|---|
| | | PCF | NCI | MVI |
| Baseline | Number of lesions | 0.66 | 0.80 | 0.50 |
| | $SUV_{total}$ | 0.67 | 0.79 | 0.52 |
| | $SUV_{max}$ | 0.50 | 0.56 | 0.56 |
| | $SUV_{mean}$ | 0.64 | 0.82 | 0.45 |
| | $SUV_{mean}$ Hetero | 0.68 | 0.84 | 0.50 |
| Follow-up | Number of lesions | 0.62 | 0.67 | 0.52 |
| | $SUV_{total}$ | 0.62 | 0.73 | 0.52 |
| | $SUV_{max}$ | 0.66 | 0.80 | 0.47 |
| | $SUV_{mean}$ | 0.57 | 0.63 | 0.53 |
| | $SUV_{mean}$ Hetero | 0.59 | 0.69 | 0.57 |
| Response | Number of lesions | 0.64 | 0.62 | 0.46 |
| | $SUV_{total}$ | 0.62 | 0.50 | 0.53 |
| | $SUV_{max}$ | 0.59 | 0.67 | 0.51 |
| | $SUV_{mean}$ | 0.62 | 0.69 | 0.48 |
| | $SUV_{mean}$ Hetero | 0.55 | 0.59 | 0.54 |
| Heterogeneity of Response | Number of CR lesions | 0.53 | 0.69 | 0.55 |
| | Number of PR lesions | 0.52 | 0.61 | 0.58 |
| | Number SD lesions | 0.64 | 0.66 | 0.58 |
| | Number of PD lesions | 0.73 | 0.70 | 0.62 |
| | Number of ND lesions | 0.72 | 0.78 | 0.56 |

TABLE 6

Univariate C-index of imaging metrics for each clinical trial obtained from Cox-Proportional Hazards regression

| Categories | Feature | Hazard Ratio | | |
|---|---|---|---|---|
| | | PCF | NCI | MVI |
| Baseline | Number of lesions | 1.49 [1.12-1.97]** | 2.06 [1.10-3.87]* | 1.05 [0.69-1.58] |
| | $SUV_{total}$ | 1.29 [1.01-1.64]* | 2.83 [1.49-5.38]** | 1.24 [0.74-2.07] |
| | $SUV_{max}$ | 1.84 [1.25-2.71]** | 2.06 [1.10-3.86]* | 1.22 [0.82-1.83] |
| | $SUV_{mean}$ | 1.30 [0.86-1.95] | 1.67 [0.97-2.90] | 1.07 [0.72-1.61] |
| | $SUV_{mean}$ Hetero | 1.70 [1.15-2.51]** | 1.59 [0.95-2.67] | 1.23 [0.78-1.93] |
| Follow-up | Number of lesions | 1.54 [1.17-2.04]** | 2.14 [1.16-3.97]* | 1.43 [0.83-2.45] |
| | $SUV_{total}$ | 1.74 [1.31-2.31]** | 4.45 [1.79-11.1]** | 1.62 [0.90-2.89] |
| | $SUV_{max}$ | 1.70 [1.20-2.42]** | 2.89 [1.40-5.96]** | 1.24 [0.72-2.12] |
| | $SUV_{mean}$ | 1.66 [1.14-2.42]** | 1.75 [0.93-3.30] | 0.78 [0.46-1.33] |
| | $SUV_{mean}$ Hetero | 1.75 [1.20-2.55]** | 1.58 [0.89-2.79] | 1.13 [0.69-1.85] |

TABLE 6-continued

Univariate C-index of imaging metrics for each clinical trial obtained from Cox-Proportional Hazards regression

| Categories | Feature | Hazard Ratio | | |
|---|---|---|---|---|
| | | PCF | NCI | MVI |
| Response | Number of lesions | 1.01 [0.72-1.41] | 1.17 [0.76-1.78] | 1.19 [0.82-1.73] |
| | $SUV_{total}$ | 1.43 [1.00-2.03]* | 1.69 [0.93-3.04] | 1.70 [0.93-3.08] |
| | $SUV_{max}$ | 1.10 [0.80-1.50] | 1.28 [0.71-2.31] | 0.74 [0.48-1.14] |
| | $SUV_{mean}$ | 1.07 [0.84-1.37] | 1.03 [0.59-1.79] | 0.74 [0.46-1.17] |
| | $SUV_{mean}$ Hetero | 1.11 [0.82-1.52] | 0.78 [0.47-1.29] | 0.71 [0.29-1.71] |
| Heterogeneity | Number of CR lesions | 1.10 [0.83-1.44] | 1.49 [0.82-2.69] | 0.99 [0.66-1.47] |
| of Response | Number of PR lesions | 1.10 [0.84-1.45] | 1.44 [0.87-2.40] | 0.90 [0.55-1.45] |
| | Number SD lesions | 1.57 [1.13-2.18]* | 1.54 [0.84-2.80] | 0.92 [0.59-1.45] |
| | Number of PD lesions | 2.75 [1.81-4.18]*** | 3.87 [1.57-5.18]** | 1.69 [1.10-2.60]* |
| | Number of ND lesions | 1.96 [1.41-2.72]*** | 2.60 [1.31-5.18]** | 2.02 [1.13-3.61]* |

Figure 1B:
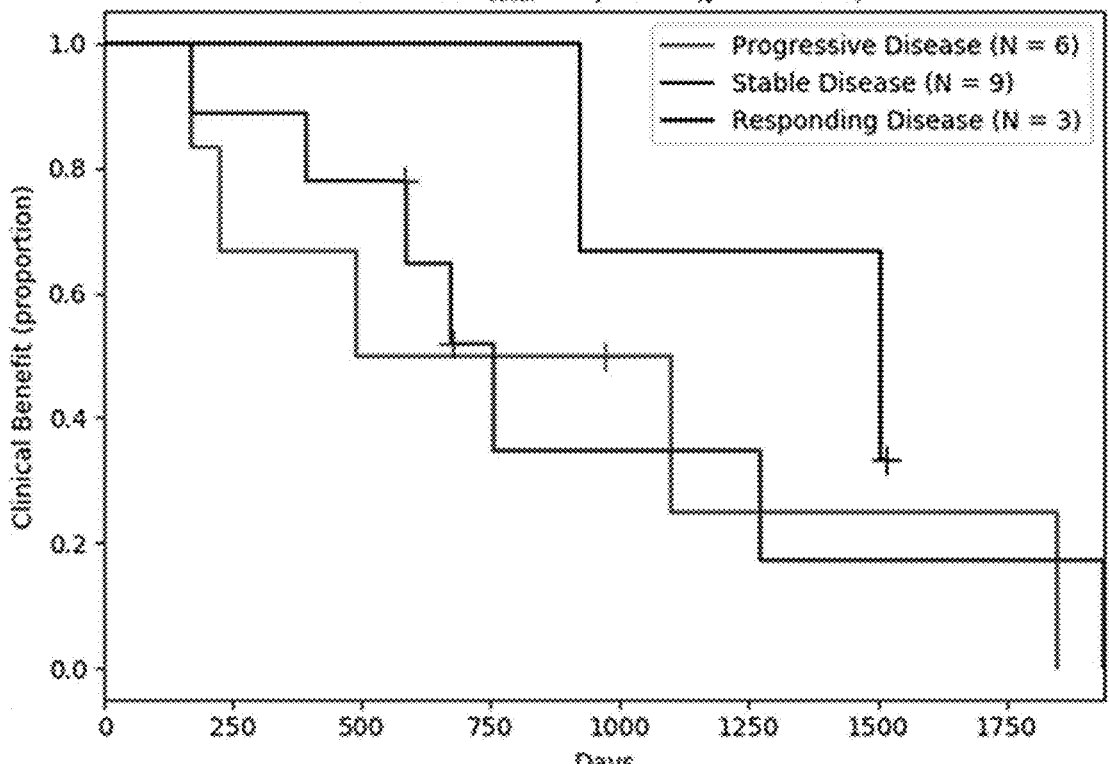
Figure 1C:
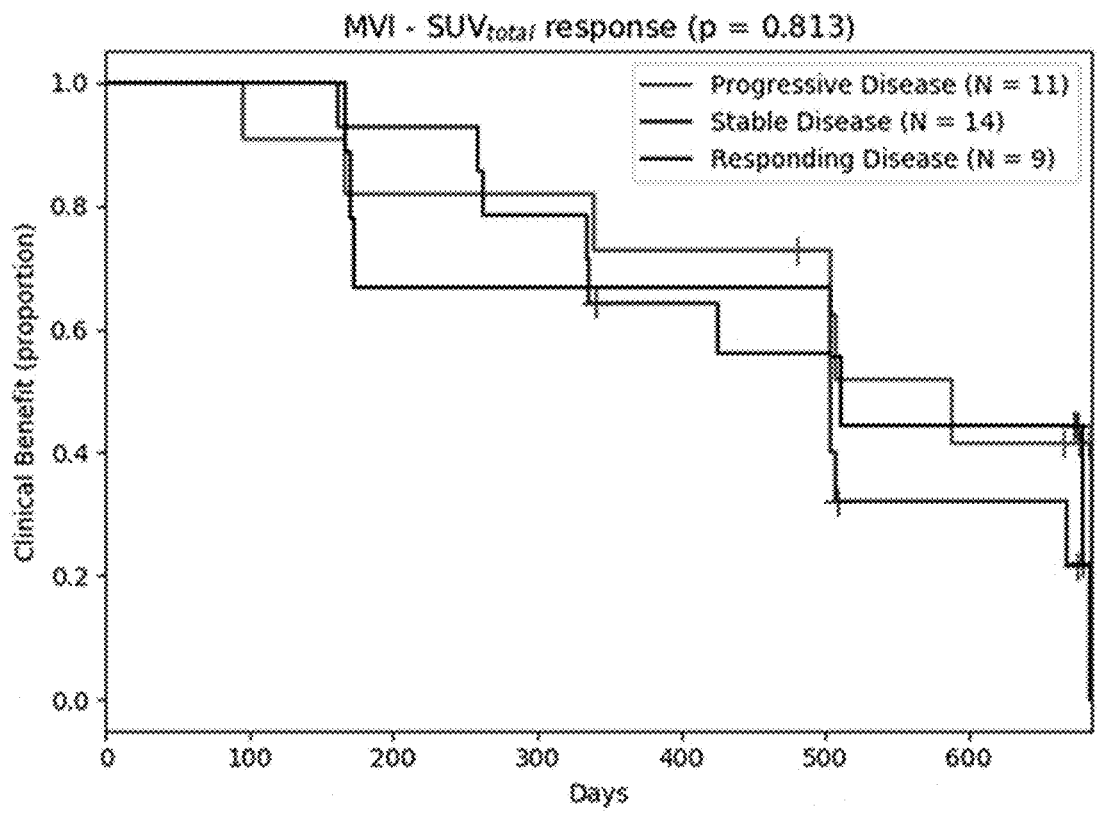

The performance of the $SUV_{total}$ classification method described in Harmon et al. (See, J Clin Oncol, 2017. 35(24): p. 2829-2837, incorporated herein by reference) is shown in FIG. 1. While this method demonstrated significant separation of clinical benefit in the PCF dataset (p=0.02), there was no significant separation (p>0.5) in the NCI or MVI datasets.

Figure 2A:
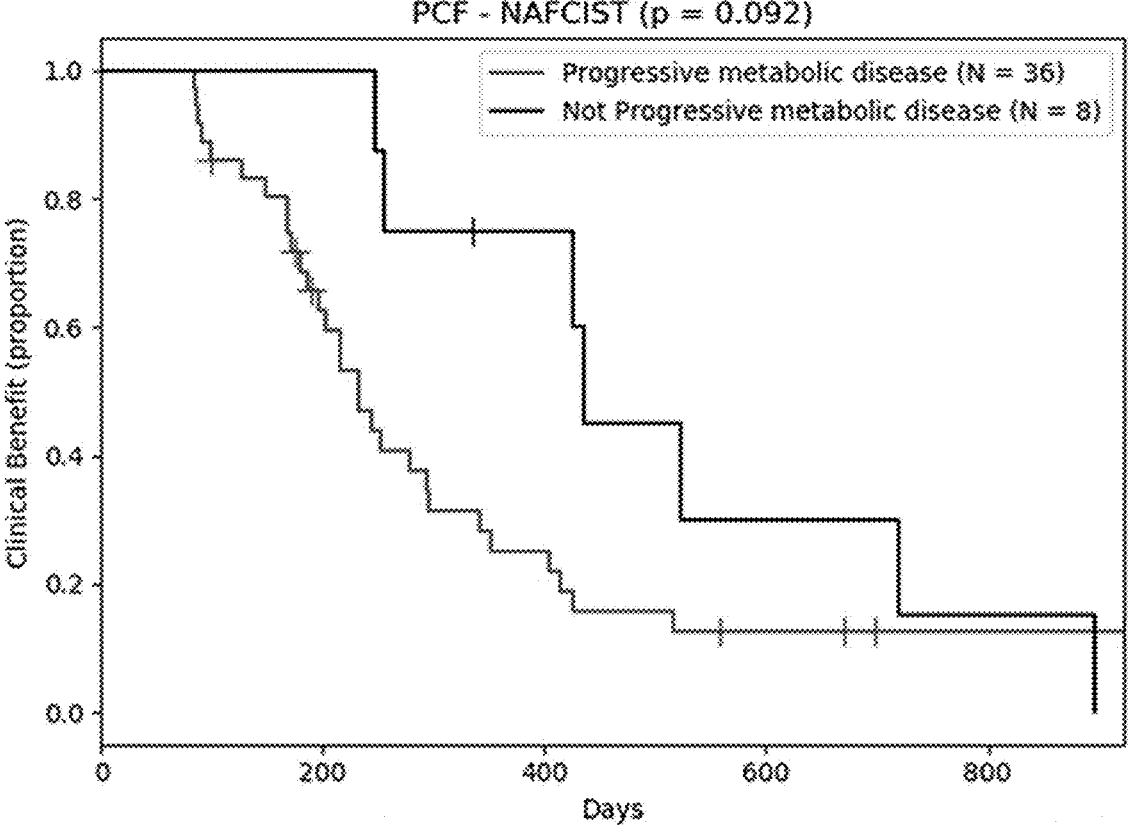
FIGS. 2A-2C are Kaplan-Meier curves for each clinical trial, as indicated, using the NAFCIST method where patients are classified as PD if there was an increase in $SUV_{peak}$ of the hottest lesion >30%, an $SUV_{total}$ increase of the two hottest lesions >75%, or any new lesions.
Figure 2B:
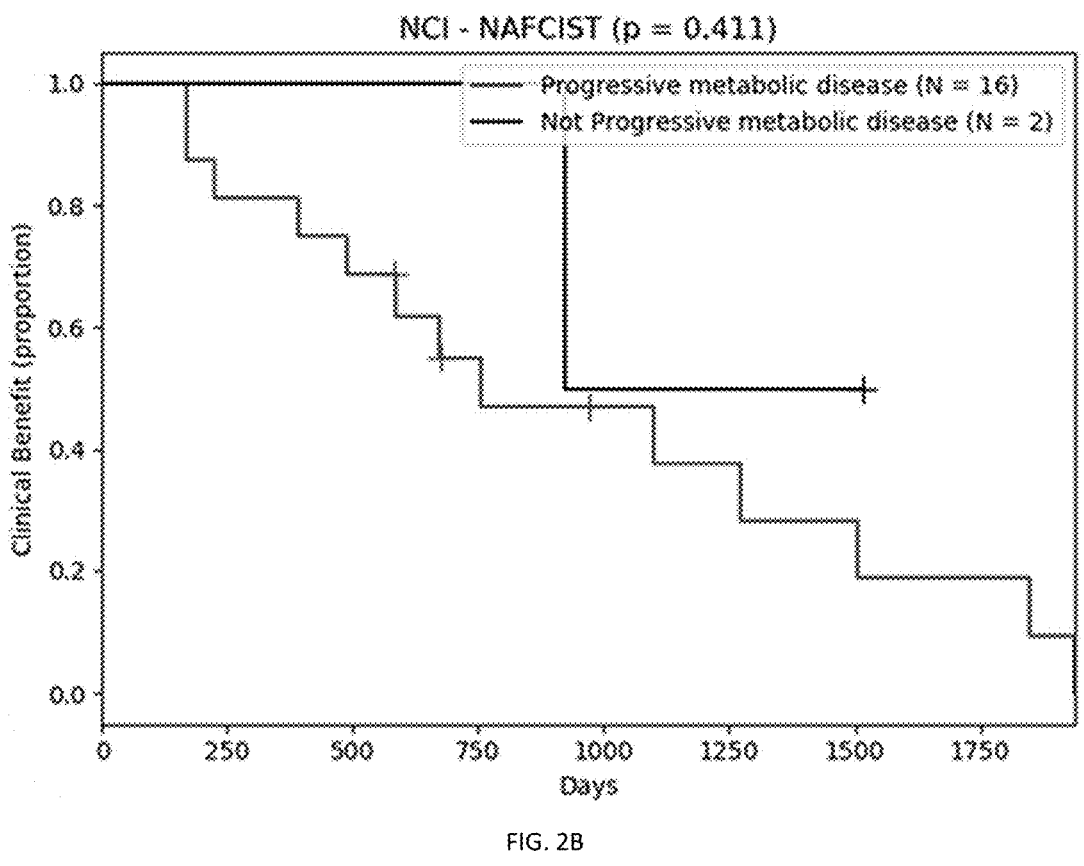
Figure 2C:
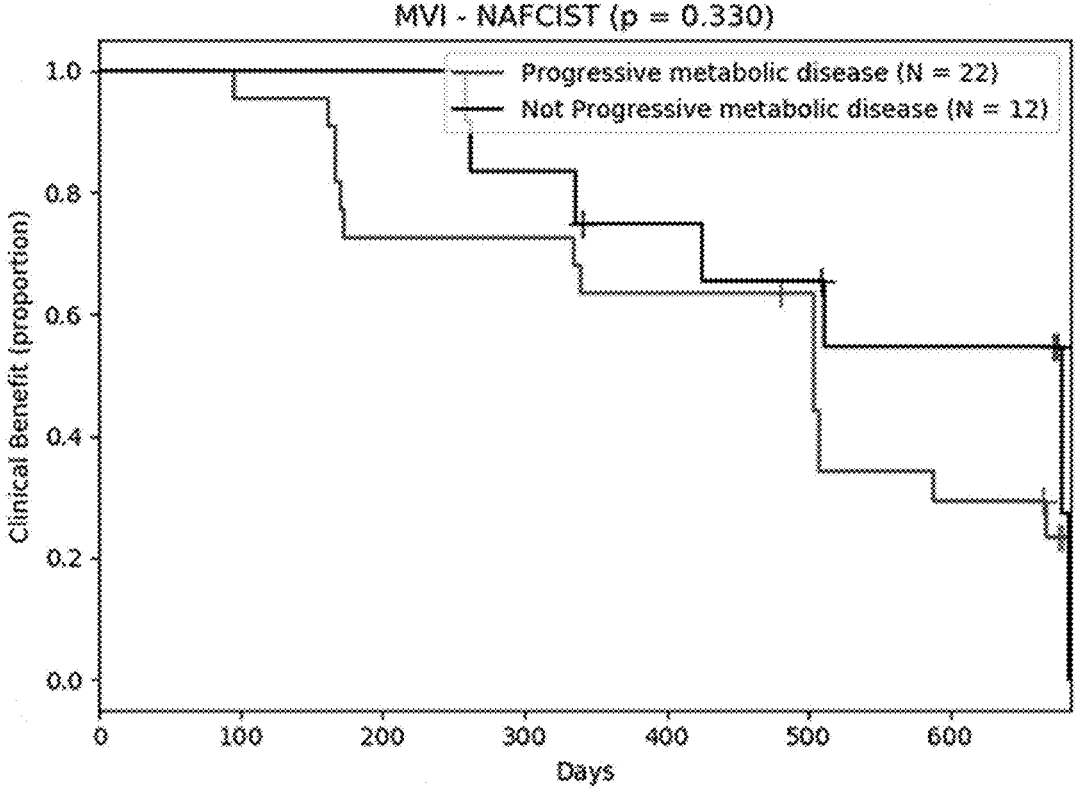

The results of applying the NAFCIST criteria to all of the datasets is shown in FIG. 2, where there was no significant separation between PD and non-PD patients. Most of the patients in this study were classified as PD using this criteria.

Figure 3A:
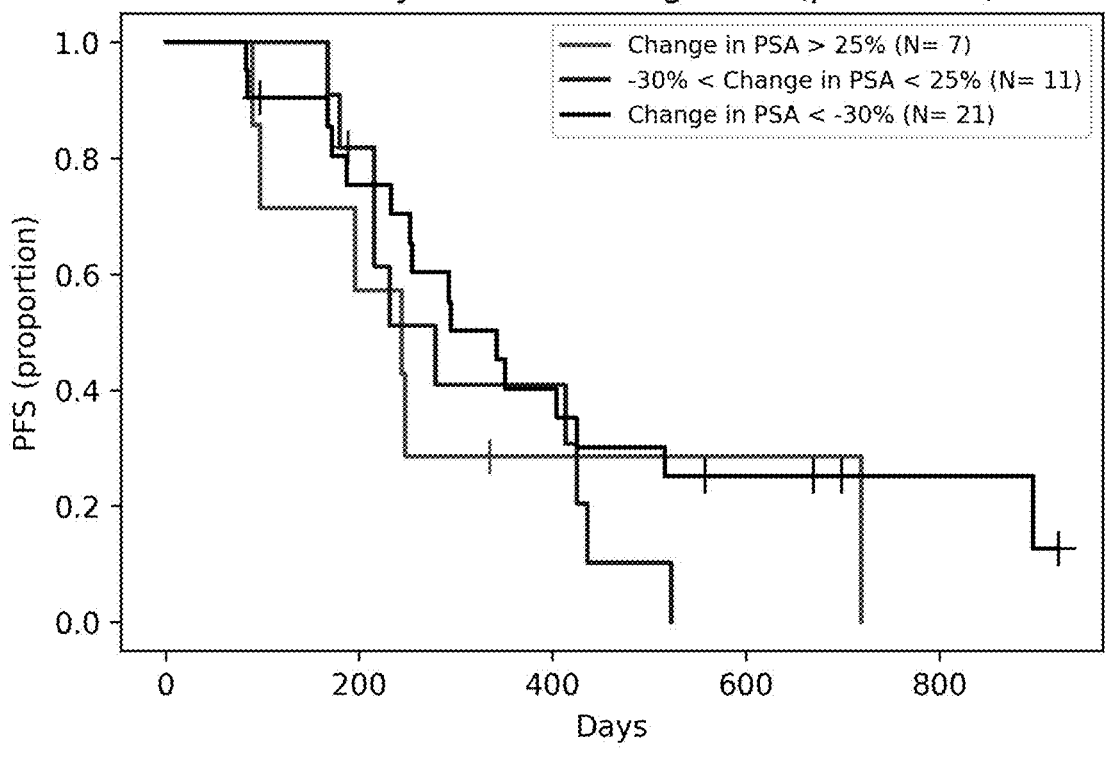
FIGS. 3A-3B are Kaplan-Meier curves for the PCF (FIG. 3A) and NCI (FIG. 3B) clinical trials, as indicated, using the PSA method where patients are classified as PD if there was an increase in PSA >25%.
Figure 3B:
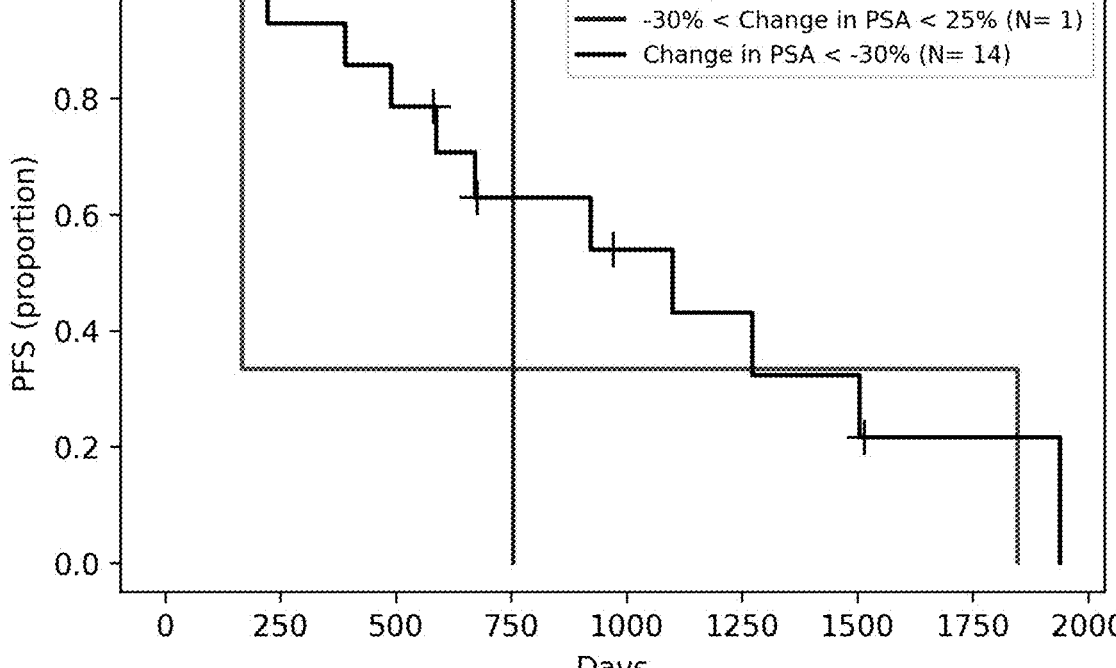

The results of applying a PSA response criteria to the PCF and NCI datasets are shown in FIG. 3, where there was no significant separation between PD and non-PD patients.

Figure 4A:
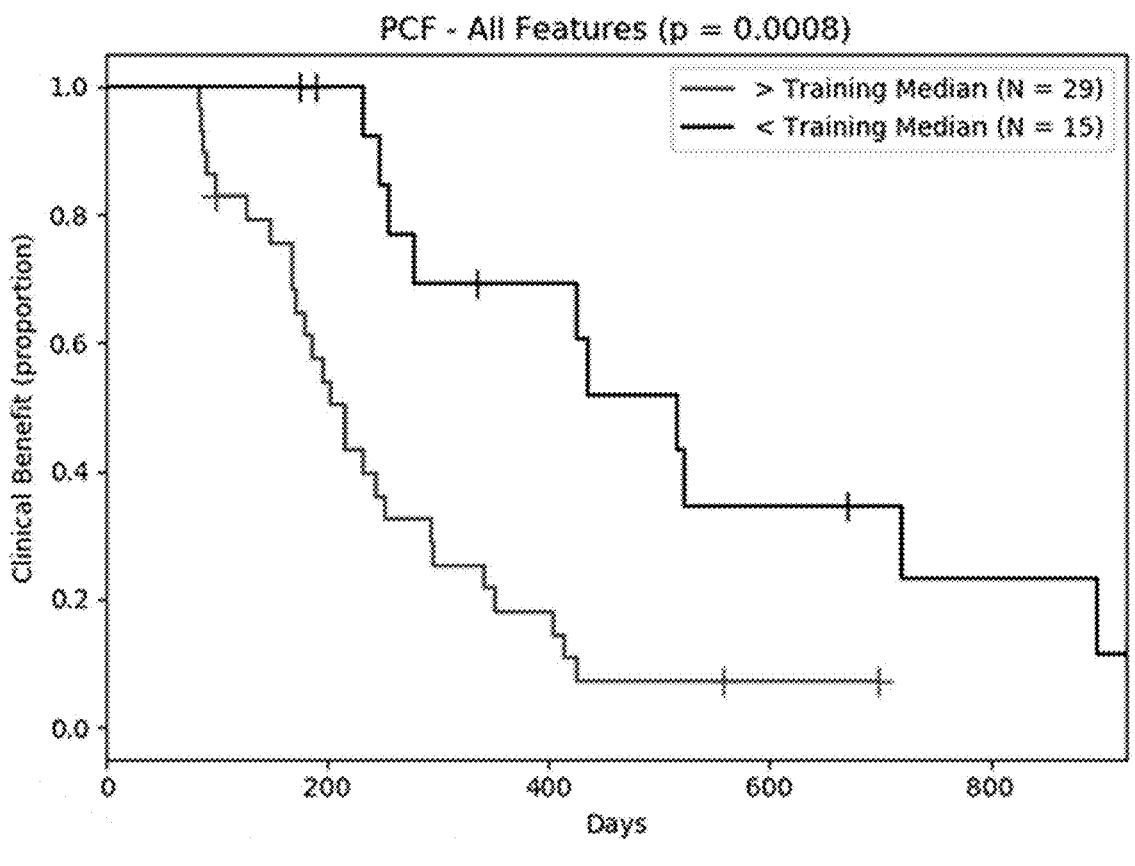
FIGS. 4A-4C are Kaplan-Meier curves showing the validation curve from the PCF data where the split was determined using a model trained on the other three datasets (FIG. 4A) and for each of the three external validation sets (FIG. 4B-4C), where the split is based on the median hazard score of a model trained on the PCF data.
Figure 4B:
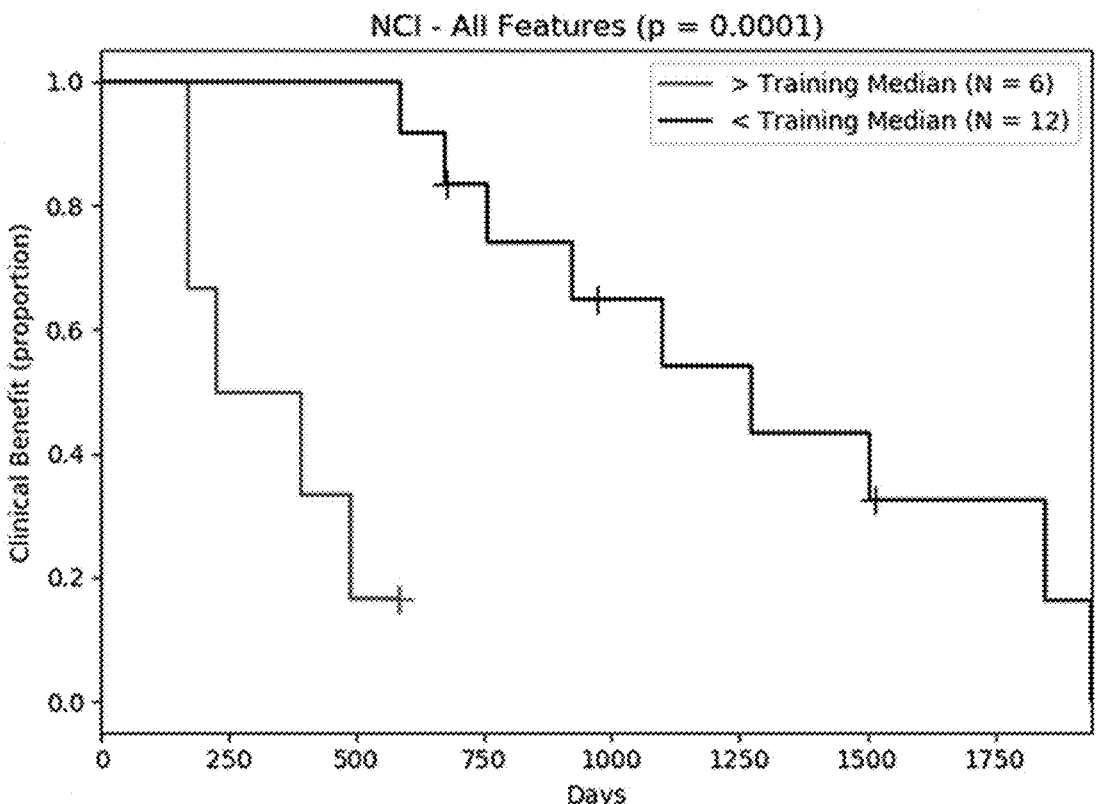
Figure 4C:
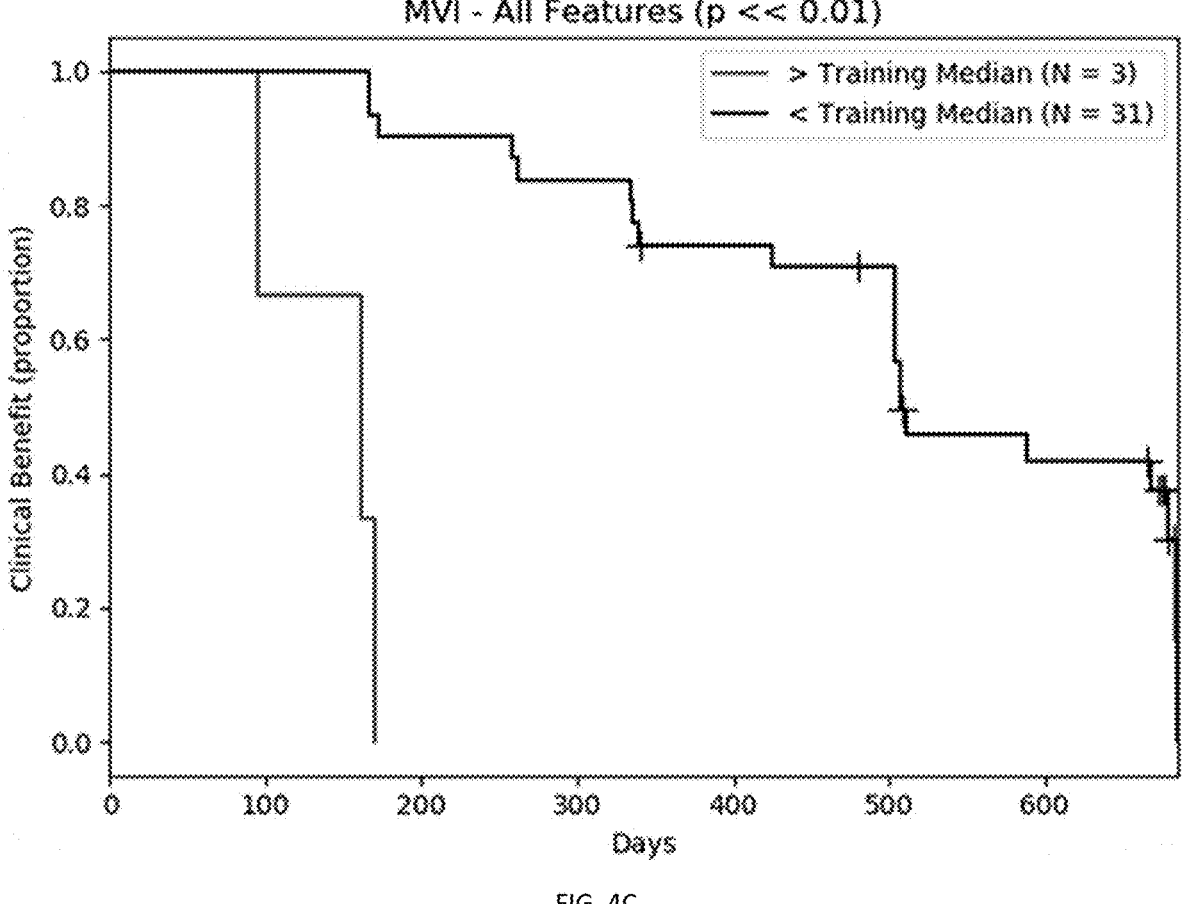

Random survival forest results with all 84 features included are shown in FIG. 4 using Kaplan-Meier curves. The median risk score from the training data was able to significantly separate patients that would be taken off drug early from patients that would have extended benefit in all the external validation datasets.

Results for varying the features seen by the RSF model are shown in Table 7. The highest performance across all validation occurred when all features were included. On average, the RSF model with only response features performed better than those of with only single timepoint measures. Using only homogeneity features, the RSF model had good performance in three of the datasets, while using heterogeneity the model was good in all external validation sets.

Figure 5:
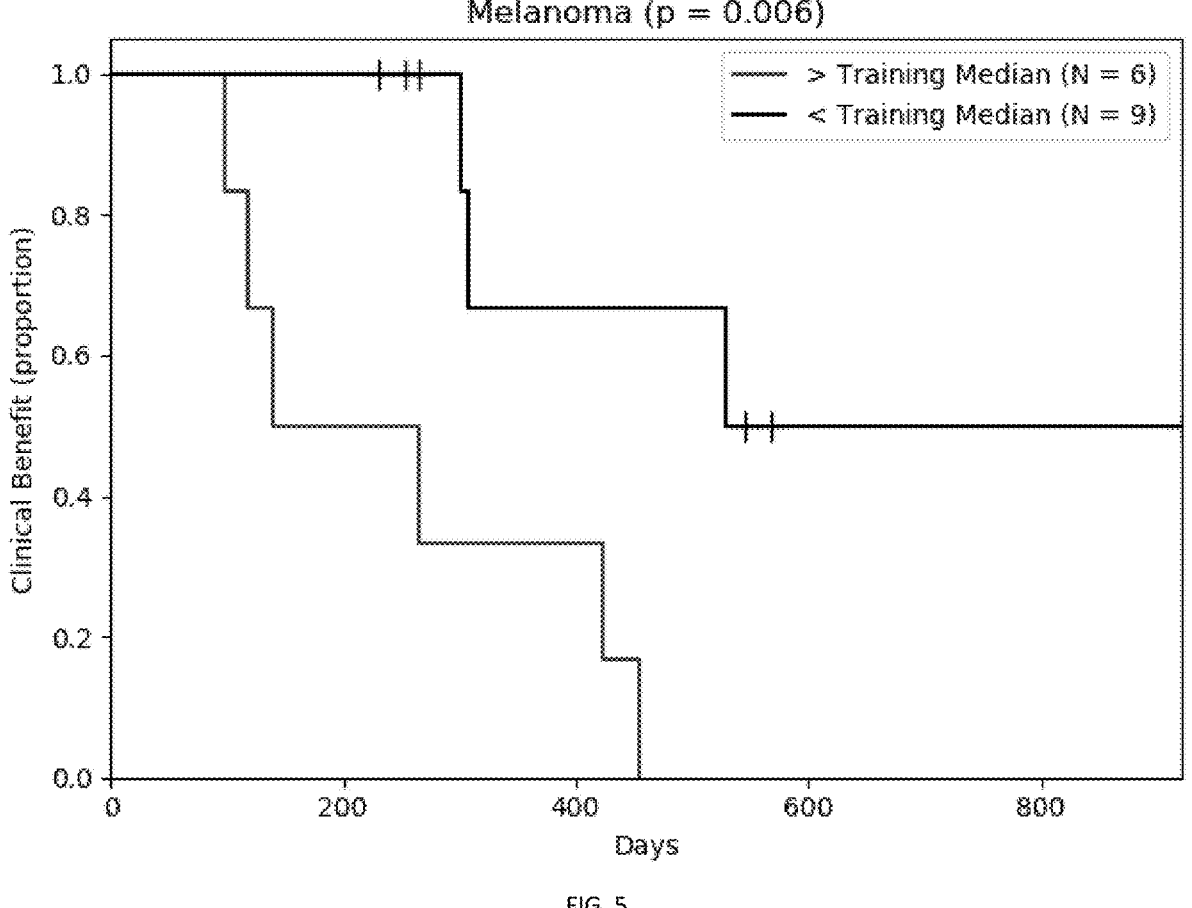
FIG. 5 are Kaplan-Meier curves showing the validation curve of an external melanoma dataset where the split is based on the median hazard score of a model trained on the PCF data.

The model trained with PCF was applied to an external dataset of 15 melanoma patients, imaged with FDG PET/CT treated with immune checkpoint inhibitors. Machine learning results are shown in FIG. 5. The median risk score from the PCF data was able to significantly separate melanoma patients that would be taken off drug early from patients that would have extended benefit in all the external validation datasets.

Figure 7:
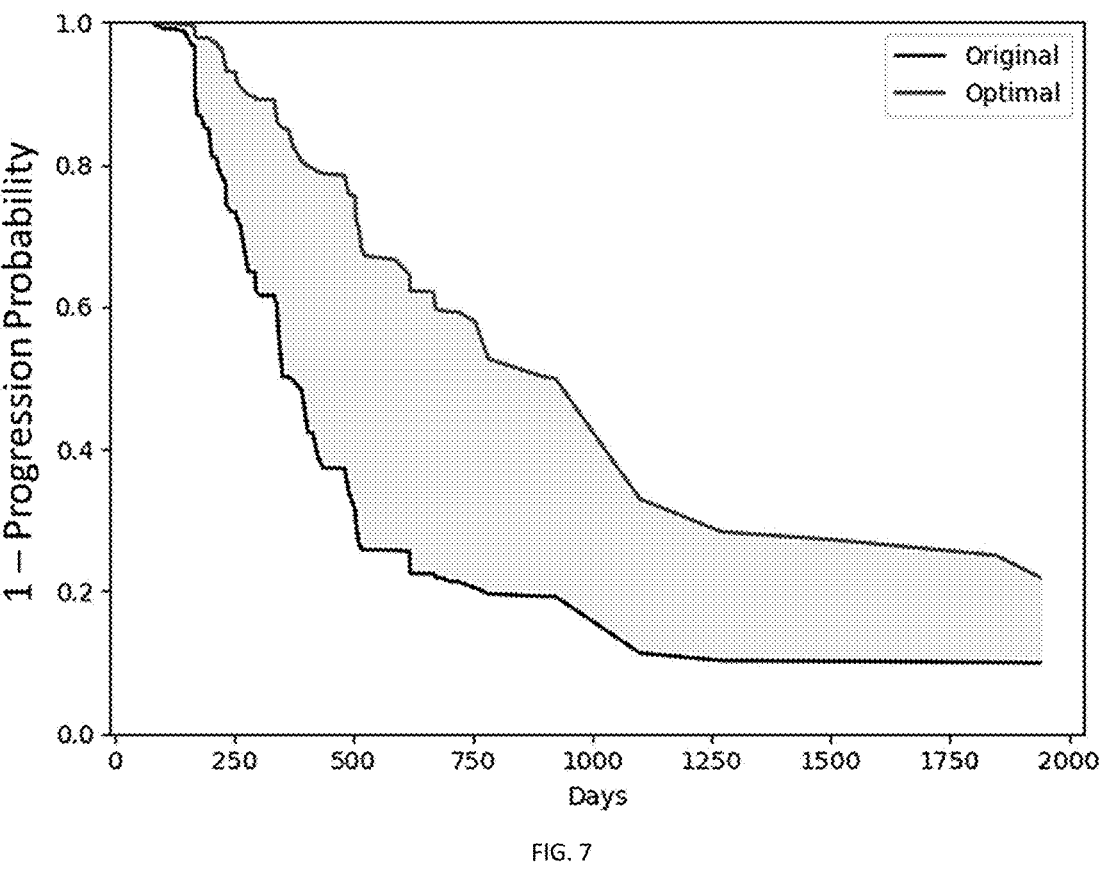
FIG. 7 shows the simulated improvement to a patient by removing the optimal selection of progressive lesions from the patient.
Figure 8:
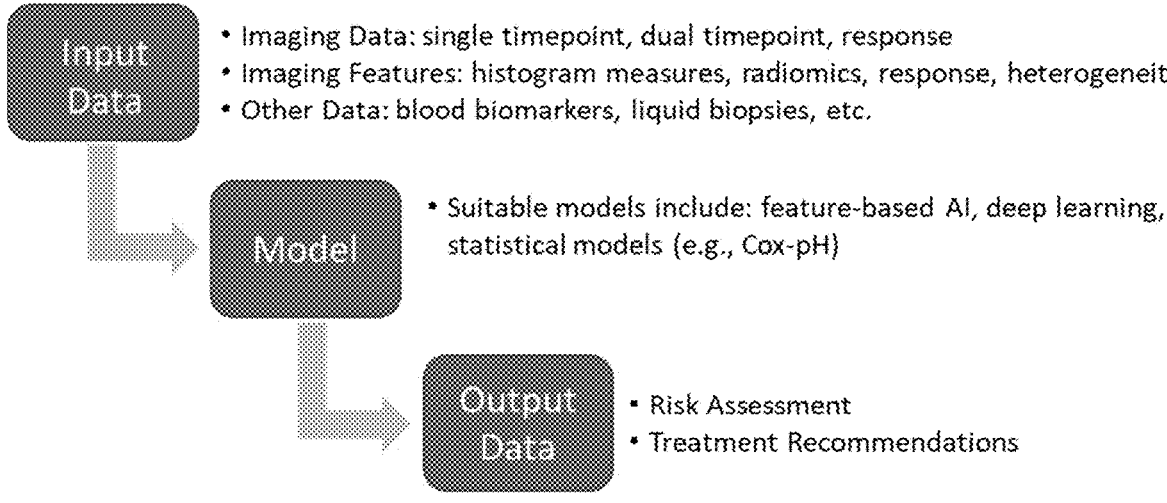
FIG. 8 shows a flow chart illustrating the method.

The model can also provide an estimate of how likely a patient will have progressed by certain times. An example of this is shown in FIG. 6. Simulation of treatment can be achieved by removing specific lesions and showing the improvements in the survival curve of the patient. FIG. 7 is an exemplary case in which a grid search was performed to find the optimal combination of 5 lesions to be removed from the patient that most improved the risk score and resulting survival curve of the patient.

All publications and patents mentioned in the present application are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the inven-

TABLE 7

Performance of random survival forest models with varied input features. The results for PCF are from a model was trained using the MDV, NCI, and MVI data together. The results from the other trials are from models trained with only the PCF data.

| Input | PCF | | NCI | | MVI | |
|---|---|---|---|---|---|---|
| Features | C-index | P-value | C-index | P-value | C-index | P-value |
| All Features | 0.78 | <0.001 | 0.80 | <0.001 | 0.70 | 0.001 |
| Baseline | 0.64 | 0.13 | 0.76 | 0.01 | 0.58 | 0.13 |
| Follow-up | 0.71 | 0.003 | 0.81 | <0.001 | 0.55 | 0.23 |
| Response | 0.76 | 0.001 | 0.69 | 0.03 | 0.71 | 0.001 |
| Homogeneity | 0.72 | 0.004 | 0.80 | <0.001 | 0.56 | 0.16 |
| Heterogeneity | 0.77 | <0.001 | 0.78 | <0.001 | 0.69 | 0.001 | tion that are obvious to those skilled in the relevant fields are intended to be within the scope of the following claims.

What is claimed is:

1. A method of assessing treatment and progression of a disease in a subject comprising:

acquiring a first and second imaging scan of the subject wherein each imaging scan utilizes a molecular imaging agent selected from a radioactive tracer, imaging probe, or contrast agent to identify and segment lesions in the subject, wherein the first scan and second imaging scan are separated by a period of time;

processing the first and second imaging scan to:

identify locations of the lesions, quantify the lesions in the subject, and calculate an imaging signal for at least one imaging feature of each lesion;

measuring changes in the at least one imaging feature directed to individual lesions, across any combination of lesions, and/or all homologous lesions in the subject between the first and second imaging scan, wherein the at least one imaging feature comprises uptake values of the molecular imaging agent comprising maximum lesion uptake ($SUV_{max}$), mean lesion uptake ($SUV_{mean}$), total lesion uptake ($SUV_{total}$), or combinations thereof; and calculating a disease treatment assessment score based on the changes in the at least one imaging feature using a machine learning model, wherein the disease treatment assessment score is a measure of the progression or regression of the disease over the period of time, wherein processing the second scan comprises calculating uptake values of the molecular imaging agent for each lesion and the disease treatment assessment score comprises a change in features that consider differences in uptake values across different lesions for homologous lesions.

2. The method of claim 1, wherein features directed to individual lesions from the first scan comprise total number of lesions, highest lesion imaging signal, average lesion imaging signal, total lesion imaging signal, size and/or volume of each lesion, and combinations thereof in the subject and wherein the features that consider differences in imaging signals across different lesions from the first scan comprise one or more textural features of maximum, mean, and total imaging signal between the different lesions.

3. The method of claim 1, wherein each lesion is classified as completely responding (iCR), partially responding (iPR), stable (iSD), progressing (iPD), or new (iNL).

4. The method of claim 1, wherein the change in features directed to individual lesions from the second scan comprise: changes in total number of lesions, maximum, mean, and total imaging signal between the individual lesions and combinations thereof in the subject and wherein the change in features that considers differences in imaging signals across different lesions from the second scan comprise: changes in one or more textural features of maximum, mean, and total imaging signal between the different lesions.

5. The method of claim 4, wherein the change in features that consider differences in imaging signals across different lesions from the second scan comprise: changes in standard deviations for maximum, mean, and total imaging signal between the different lesions in a single scan; standard deviations of the change in maximum, mean, and total imaging signal; standard deviations for skewness and kurtosis for maximum, mean, and total imaging signal; total number of lesions classified as completely responding (iCR), partially responding (iPR), stable (iSD), progressing (iPD), or new (iNL); sum of lesions classified as completely responding (iCR) and partially responding (iPR); proportion of the total number of lesions classified in each of completely responding (iCR), partially responding (iPR), stable (iSD), progressing (iPD), or new (iNL); proportion of the total number of lesions classified as completely responding (iCR) and partially responding (iPR); proportion of the total number of lesions classified as progressing (iPD) and new (iNL); standard deviations of the change in maximum, mean, and total imaging signal for lesions classified as progressing (iPD); standard deviations of the change in maximum, mean, and total imaging signal for lesions classified as partially responding (iPR); standard deviations of the mean imaging signal from first scan of lesions classified as progressing (iPD) following second scan, standard deviations of the mean imaging signal of lesions classified as progressing (iPD) and new (iNL), and the percent change between the two; standard deviations of the mean imaging signal from first scan of lesions classified as completely responding (iCR) and partially responding (iPR) following second scan, standard deviations of the mean imaging signal of lesions classified as partially responding (iPR), and the percent change between the two; maximum, mean, and total imaging signal in the subject of lesions classified as progressing (iPD) from first scan following second scan, maximum, mean, and total imaging signal in the subject of lesions from the second scan classified as progressing (iPD) and new (iNL), and the percent change between the two; maximum, mean, and total imaging signal in the subject of lesions classified as completely responding (iCR) and partially responding (iPR) from first scan following second scan, maximum, mean, and total imaging signal in the subject of lesions from the second scan classified as partially responding (iPR), and the percent change between the two; and combinations thereof.

6. The method of claim 1, wherein the features directed to individual lesions from the first scan comprise total number of lesions, maximum lesion uptake, mean lesion uptake, total lesion uptake, and combinations thereof in the subject and wherein the features that consider differences in uptake values across different lesions from the first scan comprise standard deviation, skewness, kurtosis, and combinations thereof of maximum lesion uptake, mean lesion uptake, total lesion uptake between the different lesions.

7. The method of claim 1, wherein the change in features that consider differences in uptake values across different lesions from the second scan comprise: changes in standard deviations for maximum lesion uptake, mean lesion uptake, total lesion uptake between the different lesions in a single scan; standard deviations of the change in maximum lesion uptake, mean lesion uptake, total lesion uptake; standard deviations for skewness and kurtosis for maximum lesion uptake, mean lesion uptake, total lesion uptake; total number of lesions classified as completely responding (iCR), partially responding (iPR), stable (iSD), progressing (iPD), or new (iNL); sum of lesions classified as completely responding (iCR) and partially responding (iPR); proportion of the total number of lesions classified in each of completely responding (iCR), partially responding (iPR), stable (iSD), progressing (iPD), or new (iNL); proportion of the total number of lesions classified as completely responding (iCR) and partially responding (iPR); proportion of the total number of lesions classified as progressing (iPD) and new (iNL); standard deviations of the change in maximum lesion uptake, mean lesion uptake, total lesion uptake for lesions classified as progressing (iPD); standard deviations of the change in maximum lesion uptake, mean lesion uptake, total lesion uptake for lesions classified as partially responding (iPR); standard deviations of the mean lesion uptake from first scan of lesions classified as progressing (iPD) following second scan, standard deviations of the mean lesion uptake of lesions classified as progressing (iPD) and new (iNL), and the percent change between the two; standard deviations of the mean lesion uptake from first scan of lesions classified as completely responding (iCR) and partially responding (iPR) following second scan, standard deviations of the mean lesion uptake of lesions classified as partially responding (iPR), and the percent change between the two; maximum lesion uptake, mean lesion uptake, and total lesion uptake in the subject of lesions classified as progressing (iPD) from first scan following second scan, maximum lesion uptake, mean lesion uptake, and total lesion uptake in the subject of lesions from the second scan classified as progressing (iPD) and new (iNL), and the percent change between the two; maximum lesion uptake, mean lesion uptake, and total lesion uptake in the subject of lesions classified as completely responding (iCR) and partially responding (iPR) from first scan following second scan, maximum lesion uptake, mean lesion uptake, and total lesion uptake in the subject of lesions from the second scan classified as partially responding (iPR), and the percent change between the two; and combinations thereof.

8. The method of claim 1, further comprising acquiring at least one additional imaging scan of the subject wherein the imaging scan is configured to identify and segment lesions;

processing the at least one additional imaging scan to:

identify locations of the lesions, quantify the lesions in the subject, and calculate an imaging signal for at least one imaging feature of each lesion;

determine homologous lesions between any two imaging scans and measure a change in each corresponding imaging signal, classify each lesion based on the change in each lesion; and providing a disease treatment assessment score based on evaluation of the imaging signal directed to individual lesions or for features that consider differences in imaging signals across any combination or all lesions in the subject from the at least one additional imaging scan, the change in features directed to individual lesions between any two imaging scans, the change in features that consider differences in at least one imaging signal across different lesions for homologous lesions between any two imaging scans, or a combination thereof.

9. The method of claim 1, further comprising acquiring an anatomical scan.

10. The method of claim 9, wherein the disease treatment assessment score is further based on evaluation of anatomical locations of lesions, anatomical distribution of lesions, or a combination thereof.

11. The method of claim 1, wherein the disease treatment assessment score is further based on radiomics features.

12. The method of claim 1, wherein the disease treatment assessment score is further based on biomarker data.

13. The method of claim 1, further comprising providing a disease projection analysis based on simulations of disease treatment by removal of a specific lesion, or combination of lesions, or alteration of one or more imaging features representing successful treatment of a specific lesion, or combination of lesions, from a previous imaging scan.

14. The method of claim 1, wherein the disease is cancer.

* * * * *